United States Patent
Lu et al.

(10) Patent No.: US 11,267,898 B2
(45) Date of Patent: Mar. 8, 2022

(54) ANTI-PODXL ANTIBODY MAI1738 AND ITS USE FOR CANCER TREATMENT

(71) Applicant: MedAbome, Inc., Fremont, CA (US)

(72) Inventors: Mason Lu, Fremont, CA (US); Qinhong Ma, Fremont, CA (US); Mary Q. Xu, Houston, TX (US); Jianyu Zhu, Fremont, CA (US); Yinghui Rong, San Jose, CA (US); Debashree Banerjee, Fremont, CA (US)

(73) Assignee: MEDABOME, INC., Fremont, CA (US)

( * ) Notice: Subject to any disclaimer, the term of this patent is extended or adjusted under 35 U.S.C. 154(b) by 284 days.

(21) Appl. No.: 16/687,385

(22) Filed: Nov. 18, 2019

(65) Prior Publication Data

US 2021/0139602 A1 May 13, 2021

Related U.S. Application Data

(60) Provisional application No. 62/934,760, filed on Nov. 13, 2019.

(51) Int. Cl.
| | |
|---|---|
| A61K 39/00 | (2006.01) |
| A61K 39/395 | (2006.01) |
| C12P 21/06 | (2006.01) |
| C07H 21/04 | (2006.01) |
| C12N 1/20 | (2006.01) |
| C12N 15/74 | (2006.01) |
| C07K 16/28 | (2006.01) |

(52) U.S. Cl.
CPC .... *C07K 16/2896* (2013.01); *C07K 2317/565* (2013.01); *C07K 2317/622* (2013.01); *C07K 2317/92* (2013.01)

(58) Field of Classification Search
None
See application file for complete search history.

(56) References Cited

U.S. PATENT DOCUMENTS

2019/0153471 A1* 5/2019 Paul .............. C07K 16/00

FOREIGN PATENT DOCUMENTS

| WO | WO-2008079361 A2 * | 7/2008 | .............. C07K 16/24 |
| WO | WO2017114204 | 7/2017 | |
| WO | WO-2017114204 A1 * | 7/2017 | ........... G01N 33/577 |

OTHER PUBLICATIONS

Dong-qing et al. MS17-38 mAb targeting of PODXL-v2 inhibits gastric cancer growth and metastasis. Madridge J Cancer Stud Res. 2016, Abstract. Apr. 4-6, 2016. (Year: 2016).*
Brown et al. Tolerance of single, but not multiple, amino acid replacements in antibody VH CDR2: a means of minimizing B cell wastage from somatic hypermutation? J. Immuno. May 1996, 3285-91. (Year: 1996).*
Vajdos et al. Comprehensive functional maps of the antigen-binding site of an anti-ErbB2 antibody obtained with shotgun scanning mutagenesis. J. Mol. Biol. Jul. 5, 2002, 320(2):415-28. (Year: 2002).*
G D. et al., "MS17-38 mAb targeting of PODXL-V2 inhibits gastric cancer growth and metastasis" Madridge J Cancer Stud Res. 2016 MJCSR an open access journal; p. 80 (2016).

* cited by examiner

*Primary Examiner* — Maher M Haddad
(74) *Attorney, Agent, or Firm* — Eric P. Mirable, JD, LLM

(57) ABSTRACT

The present invention provides a therapeutic agent for the treatment, prevention and diagnosis of cancers associated with cells that overexpressing podocalyxin-like protein precursor isoform 2 (PODXL-v2) and its variants with deletion of N-terminal serine and proline residues, on the cell surface, including gastric cancers, squamous cell carcinoma of the stomach, gastric adenocarcinoma, small cell carcinoma of the stomach, gastric squamous cell carcinoma, gastric carcinoid tumors, stomach and duodenal cancers, gliobastoma, prostate cancer, urothelial bladder cancer, pancreatic cancer, esophageal cancer, colorectal cancer, ovarian cancer, liver cancer. The agent is based on the amino acid sequences of the novel light chain variable regions of an anti-PODXL-v2 monoclonal antibody (mAb), MAb1738, that can functionally inhibit the proliferation of several human cancer cell lines and the growth and metastasis of gastric cancer in mouse models.

20 Claims, 19 Drawing Sheets

Specification includes a Sequence Listing.

Fig. 2A

```
PODXL-v1       GACGACACGATGCGCTGCCGCTGCCTGCCGCTGGCGCTCTCGGCGCTGCTGCTACTGTTGTCAACGCCG      60
PODXL-v2       GACGACACGATGCGCTGCCGCTGCCTGCCGCTGGCGCTCTCGGCGCTGCTGCTACTGTTGTCAACGCCG      60
PODXL-v2-Del   GACGACACGATGCGCTGCCGCTGCCTGCCGCTGGCGCTCTCGGCGCTGCTGCTACTGTTGTCAACGCCG      60
               *******************************************************************

PODXL-v1       CCGCTGCTGCCGTCGTCGCCGTCGCCGTCGCCGTCGCCCTCGCCCTCCCAGAATGCAACCCAGACT     120
PODXL-v2       CCGCTGCTGCCGTCGTCGCCGTCGCCGTCGCCGTCGCCCTCGCCCTCCCAGAATGCAACCCAGACT     120
PODXL-v2-Del   CCGCTGCTGCCGTCGTCGCCGTCGCCGTCGCCGTCGCCg------TCGCCGTCGCCCTCCCAGAATGCAACCCAGACT     114
               ******************************      ******

PODXL-v1       ACTACGGACTCATCTAACAAAACAGCCCAGCAGAGCACAGTCCCCACTTCCAAGGCCATCCAGTGTCACCATCATGGCT     180
PODXL-v2       ACTACGGACTCATCTAACAAAACAGCCCAGCAGAGCACAGTCCCCACTTCCAAGGCCATCCAGTGTCACCATCATGGCT     180
PODXL-v2-Del   ACTACGGACTCATCTAACAAAACAGCCCAGCAGAGCACAGTCCCCACTTCCAAGGCCATCCAGTGTCACCATCATGGCT     174
               *******************************************************************

PODXL-v1       ACAGATACAGCCCAGCAGAGCACAGTCCCCACTTCCAAGGCCAACGAAATCTTGGCCTCG     240
PODXL-v2       ACAGATACAGCCCAGCAGAGCACAGTCCCCACTTCCAAGGCCAACGAAATCTTGGCCTCG     240
PODXL-v2-Del   ACAGATACAGCCCAGCAGAGCACAGTCCCCACTTCCAAGGCCAACGAAATCTTGGCCTCG     234
               *******************************************************************

PODXL-v1       GTCAAGGCCGACCACCCTTGGTGTATCCAGTGACTCACCGGGACTACAACCCTGGCTCAG     300
PODXL-v2       GTCAAGGCCGACCACCCTTGGTGTATCCAGTGACTCACCGGGACTACAACCCTGGCTCAG     300
PODXL-v2-Del   GTCAAGGCCGACCACCCTTGGTGTATCCAGTGACTCACCGGGACTACAACCCTGGCTCAG     294
               *******************************************************************

PODXL-v1       CAAGTCTCAGGCCCAGTCAACACTACCGTGGCTAGAGGAGGCGGCTCAGGCAACCCTACT     360
PODXL-v2       CAAGTCTCAGGCCCAGTCAACACTACCGTGGCTAGAGGAGGCGGCTCAGGCAACCCTACT     360
PODXL-v2-Del   CAAGTCTCAGGCCCAGTCAACACTACCGTGGCTAGAGGAGGCGGCTCAGGCAACCCTACT     354
               *******************************************************************
```

Fig. 2B

```
PODXL-v1       ACCACCATCGAGAGCCCCAAGAGCACAAAAAGTGCAGACACCACTACAGTTGCAACCTCC    420
PODXL-v2       ACCACCATCGAGAGCCCCAAGAGCACAAAAAGTGCAGACACCACTACAGTTGCAACCTCC    420
PODXL-v2-Del   ACCACCATCGAGAGCCCCAAGAGCACAAAAAGTGCAGACACCACTACAGTTGCAACCTCC    414
               ************************************************************

PODXL-v1       ACAGCCACAGCTAAACCTAACACCACAAGCAGCCAGAATGGAGCAGAAGATACAACAAAC    480
PODXL-v2       ACAGCCACAGCTAAACCTAACACCACAAGCAGCCAGAATGGAGCAGAAGATACAACAAAC    480
PODXL-v2-Del   ACAGCCACAGCTAAACCTAACACCACAAGCAGCCAGAATGGAGCAGAAGATACAACAAAC    474
               ************************************************************

PODXL-v1       TCTGGGGAAAAGCAGCCACAGTGTGACCACAGACCTCACATCCACTAAGGCAGAACAT    540
PODXL-v2       TCTGGGGAAAAGCAGCCACAGTGTGACCACAGACCTCACATCCACTAAGGCAGAACAT    540
PODXL-v2-Del   TCTGGGGAAAAGCAGCCACAGTGTGACCACAGACCTCACATCCACTAAGGCAGAACAT    534
               ************************************************************

PODXL-v1       CTGACGACCCCTCACCCTACAAGTCCACTTAGCCCCGACAACCCACTTCGACGCATCCT    600
PODXL-v2       CTGACGACCCCTCACCCTACAAGTCCACTTAGCCCCGACAACCCACTTCGACGCATCCT    600
PODXL-v2-Del   CTGACGACCCCTCACCCTACAAGTCCACTTAGCCCCGACAACCCACTTCGACGCATCCT    594
               ************************************************************

PODXL-v1       GTGGCCACCCCAACAAGCTCGGGACATGACCATCTTATGAAAATTCAAGCAGTTCAAGC    660
PODXL-v2       GTGGCCACCCCAACAAGCTCGGGACATGACCATCTTATGAAAATTCAAGCAGTTCAAGC    660
PODXL-v2-Del   GTGGCCACCCCAACAAGCTCGGGACATGACCATCTTATGAAAATTCAAGCAGTTCAAGC    654
               ************************************************************

PODXL-v1       ACTGTGGCTATCCCTGGCTACACCTTCACAAGCCCGGGATGACCACCCTACTAGAG       720
PODXL-v2       ACTGTGGCTATCCCTGGCTACACCTTCACAAGCCCGGGATGACCACCACCCTA------   714
PODXL-v2-Del   ACTGTGGCTATCCCTGGCTACACCTTCACAAGCCCGGGATGACCACCACCCTA------   708
               ****************************************************
```

Fig. 2C

```
PODXL-v1      ACAGTGTTTCACCATGTCAGCCAGGCTGGTCTTGAACTCCCTGACCTCGGGTGATCTGCCC    780
PODXL-v2      ------------------------------------------------------------    714
PODXL-v2-Del  ------------------------------------------------------------    708

PODXL-v1      ACCTTGGCCTCCCAAAGTGCTGGGATTACAGGCGTCATCGGTTATCTCGCAAAGAACTCAA    840
PODXL-v2      ---------------------------CCGTCATCGGTTATCTCGCAAAGAACTCAA       744
PODXL-v2-Del  ---------------------------CCGTCATCGGTTATCTCGCAAAGAACTCAA       736
                                         *******************************

PODXL-v1      CAGACCTCCAGTCAGATGCCAGCCAGCTCTACGGCAAGCTCTACCCCTTCCTCCCAGGAGACAGTGCAG    900
PODXL-v2      CAGACCTCCAGTCAGATGCCAGCCAGCTCTACGGCCAGCCCCTTCCTCCCAGGAGACAGTGCAG        804
PODXL-v2-Del  CAGACCTCCAGTCAGATGCCAGCCAGCTCTACGGCCAGCCCCTTCCTCCCAGGAGACAGTGCAG        798
              *********************************      ************************

PODXL-v1      CCCACGAGCCCGGCAACGGCATTGAGAACACCTACCCTGCCAGAGACCATGAGCTCCAGC    960
PODXL-v2      CCCACGAGCCCGGCAACGGCATTGAGAACACCTACCCTGCCAGAGACCATGAGCTCCAGC    864
PODXL-v2-Del  CCCACGAGCCCGGCAACGGCATTGAGAACACCTACCCTGCCAGAGACCATGAGCTCCAGC    858
              ************************************************************

PODXL-v1      CCCACAGCAGCATCAACTACCCCACCGATACCCCAAAACACCTTCTCCCACTGTGGCTCAT    1020
PODXL-v2      CCCACAGCAGCATCAACTACCCCACCGATACCCCAAAACACCTTCTCCCACTGTGGCTCAT     924
PODXL-v2-Del  CCCACAGCAGCATCAACTACCCCACCGATACCCCAAAACACCTTCTCCCACTGTGGCTCAT     918
              ************************************************************

PODXL-v1      GAGAGTAACTGGGCAAAGTGTGAGGATCTTGAGACACAGAGACACAGAGTGAGAAGCAGCTC    1080
PODXL-v2      GAGAGTAACTGGGCAAAGTGTGAGGATCTTGAGACACAGAGACACAGAGTGAGAAGCAGCTC     984
PODXL-v2-Del  GAGAGTAACTGGGCAAAGTGTGAGGATCTTGAGACACAGAGACACAGAGTGAGAAGCAGCTC     978
              ************************************************************
```

Fig. 2D

```
PODXL-v1      GTCCTGAACCTCACAGGAAACACCCTCTGTGCAGGGGCGCTTCGGATGAGAAATTGATC    1140
PODXL-v2      GTCCTGAACCTCACAGGAAACACCCTCTGTGCAGGGGCGCTTCGGATGAGAAATTGATC    1044
PODXL-v2-Del  GTCCTGAACCTCACAGGAAACACCCTCTGTGCAGGGGCGCTTCGGATGAGAAATTGATC    1038
              ************************************************************

PODXL-v1      TCACTGATATGCCGAGCAGTCAAAGCCACCTTCAACCCGGCCAAGATAAGTGCGGCATA    1200
PODXL-v2      TCACTGATATGCCGAGCAGTCAAAGCCACCTTCAACCCGGCCAAGATAAGTGCGGCATA    1104
PODXL-v2-Del  TCACTGATATGCCGAGCAGTCAAAGCCACCTTCAACCCGGCCAAGATAAGTGCGGCATA    1098
              ************************************************************

PODXL-v1      CGGCTGGCATCTGTTCCAGGAAGTCAGACCGTGGTCGTCAAAGAAATCACTATTCACACT    1260
PODXL-v2      CGGCTGGCATCTGTTCCAGGAAGTCAGACCGTGGTCGTCAAAGAAATCACTATTCACACT    1164
PODXL-v2-Del  CGGCTGGCATCTGTTCCAGGAAGTCAGACCGTGGTCGTCAAAGAAATCACTATTCACACT    1153
              ************************************************************

PODXL-v1      AAGCTCCCTGCCAAGGATGTGTACGAGCGGCTGAAGGACAAATGGGATGAACTAAAGGAG    1320
PODXL-v2      AAGCTCCCTGCCAAGGATGTGTACGAGCGGCTGAAGGACAAATGGGATGAACTAAAGGAG    1224
PODXL-v2-Del  AAGCTCCCTGCCAAGGATGTGTACGAGCGGCTGAAGGACAAATGGGATGAACTAAAGGAG    1218
              ************************************************************

PODXL-v1      GCAGGGGTCAGTGACATGAAGCTAGGGGACCAGGGCCACCGGAGGAGGCCGAGGACCGC    1380
PODXL-v2      GCAGGGGTCAGTGACATGAAGCTAGGGGACCAGGGCCACCGGAGGAGGCCGAGGACCGC    1284
PODXL-v2-Del  GCAGGGGTCAGTGACATGAAGCTAGGGGACCAGGGCCACCGGAGGAGGCCGAGGACCGC    1278
              ************************************************************

PODXL-v1      TTCAGCATGCCCCTCATCATCACCATCGTCTGCATGGCATCATTCCTGCTCCTCGTGGCG    1440
PODXL-v2      TTCAGCATGCCCCTCATCATCACCATCGTCTGCATGGCATCATTCCTGCTCCTCGTGGCG    1344
PODXL-v2-Del  TTCAGCATGCCCCTCATCATCACCATCGTCTGCATGGCATCATTCCTGCTCCTCGTGGCG    1338
              ************************************************************
```

Fig. 2E

```
PODXL-v1        GCCCTCTATGGCTGCTGCCACCAGCGCCTCTCCCAGAGGAAGGACCAGCAGCGGCTAACA    1500
PODXL-v2        GCCCTCTATGGCTGCTGCCACCAGCGCCTCTCCCAGAGGAAGGACCAGCAGCGGCTAACA    1404
PODXL-v2-Del    GCCCTCTATGGCTGCTGCCACCAGCGCCTCTCCCAGAGGAAGGACCAGCAGCGGCTAACA    1398
                ************************************************************

PODXL-v1        GAGGAGCTGCAGACAGTGGAGAATGGTTACCATGACAACCCAACACTGGAAGTGATGGAG    1560
PODXL-v2        GAGGAGCTGCAGACAGTGGAGAATGGTTACCATGACAACCCAACACTGGAAGTGATGGAG    1464
PODXL-v2-Del    GAGGAGCTGCAGACAGTGGAGAATGGTTACCATGACAACCCAACACTGGAAGTGATGGAG    1458
                ************************************************************

PODXL-v1        ACCTCTTCTGAGATGCAGGAGAAGAAGGTGGTCAGCCTCAACGGGGAGCTGGGGGACAGC    1620
PODXL-v2        ACCTCTTCTGAGATGCAGGAGAAGAAGGTGGTCAGCCTCAACGGGGAGCTGGGGGACAGC    1524
PODXL-v2-Del    ACCTCTTCTGAGATGCAGGAGAAGAAGGTGGTCAGCCTCAACGGGGAGCTGGGGGACAGC    1518
                ************************************************************

PODXL-v1        TGGATCGTCCCCTCTGGACAACCTGACCAAGGACGACCTGGATGAGGAGGAAGACACACAC    1680
PODXL-v2        TGGATCGTCCCCTCTGGACAACCTGACCAAGGACGACCTGGATGAGGAGGAAGACACACAC    1584
PODXL-v2-Del    TGGATCGTCCCCTCTGGACAACCTGACCAAGGACGACCTGGATGAGGAGGAAGACACACAC    1578
                ************************************************************

PODXL-v1        CTCTAG  1686  (SEQ ID NO.: 10)
PODXL-v2        CTCTAG  1590  (SEQ ID NO.: 11)
PODXL-v2-Del    CTCTAG  1584  (SEQ ID NO.: 12)
                ******
```

| Loading Sample ID | Sample ID | Conc. (nM) | Response | KD (M) | KD Error | Full X^2 | Full R^2 |
|---|---|---|---|---|---|---|---|
| MAI1738 | rPODXL-v2-Del-Fc | 555.6 | 0.1237 | 1.58E-09 | 5.17E-11 | 1.028147 | 0.993722 |
| MAI1738 | rPODXL-v2-Del-Fc | 277.8 | 0.1097 | 1.58E-09 | 5.17E-11 | 1.028147 | 0.993722 |
| MAI1738 | rPODXL-v2-Del-Fc | 138.9 | 0.093 | 1.58E-09 | 5.17E-11 | 1.028147 | 0.993722 |
| MAI1738 | rPODXL-v2-Del-Fc | 69.4 | 0.0747 | 1.58E-09 | 5.17E-11 | 1.028147 | 0.993722 |

Fig. 6
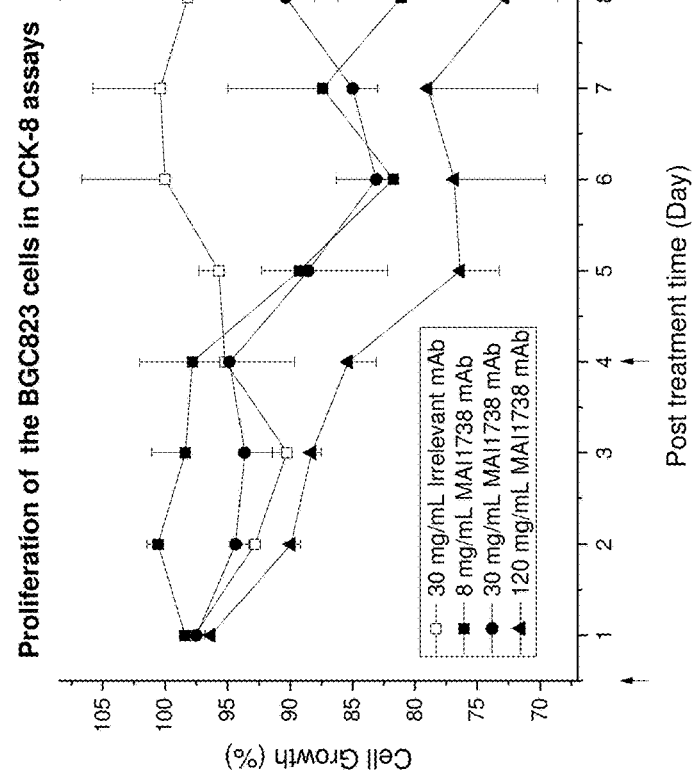
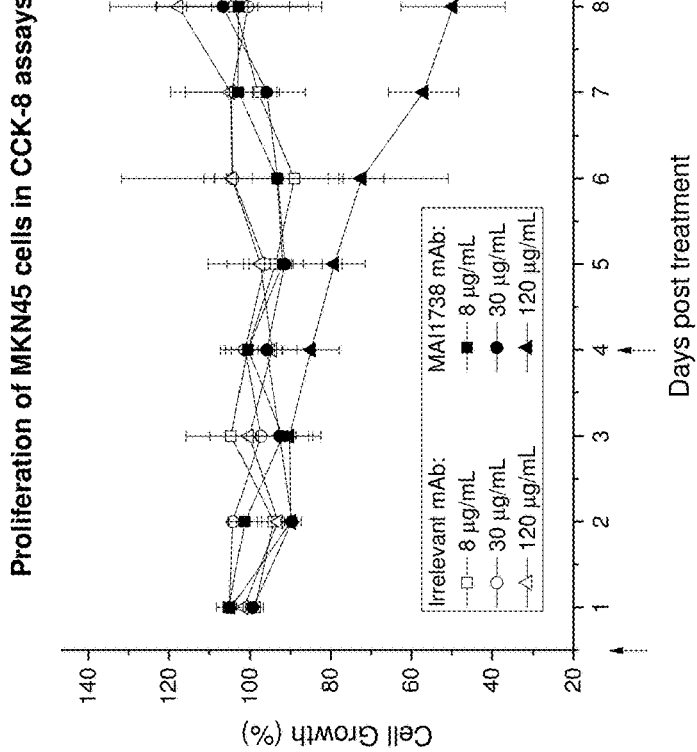

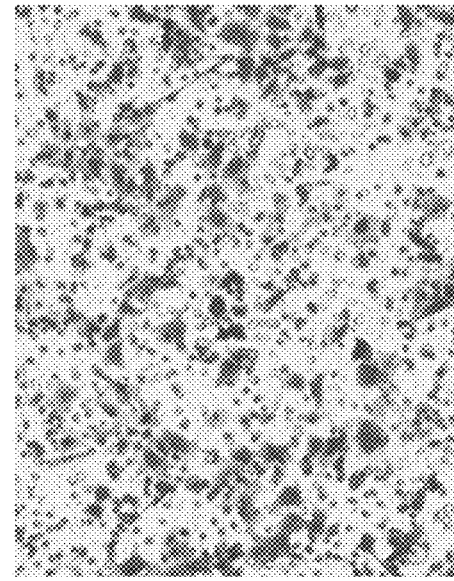
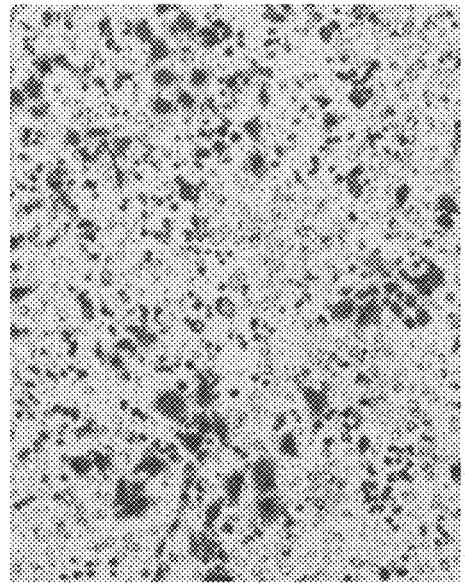
Fig. 7B

Fig. 8A
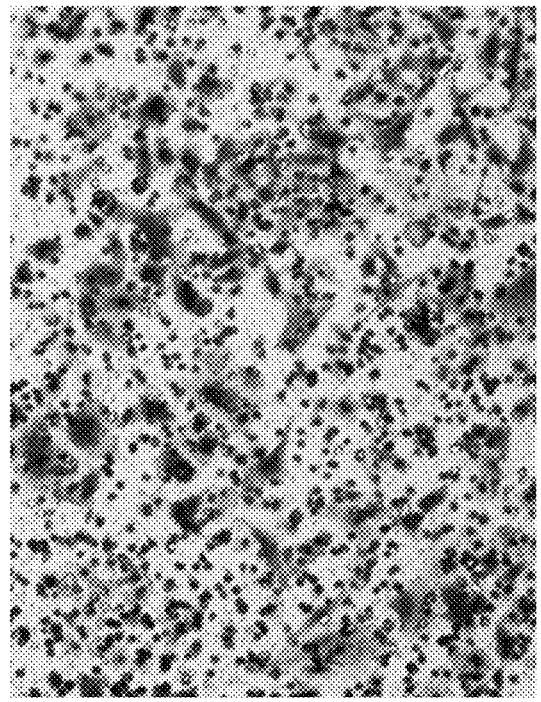
Negative control siRNA
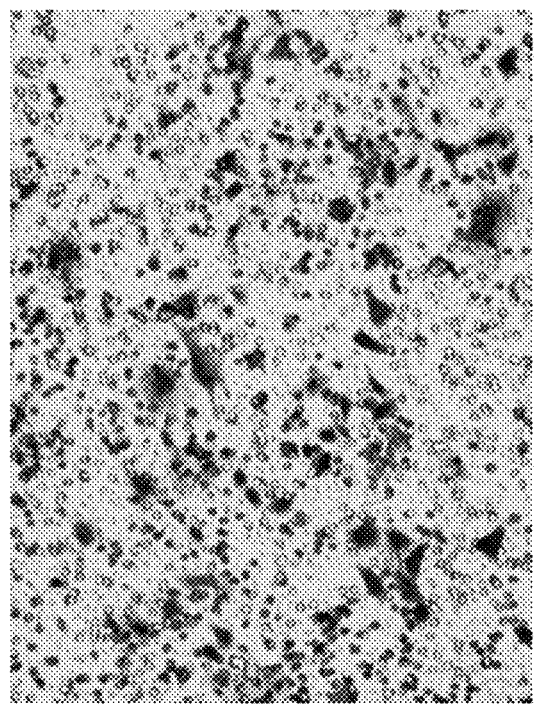
PODXL siRNA

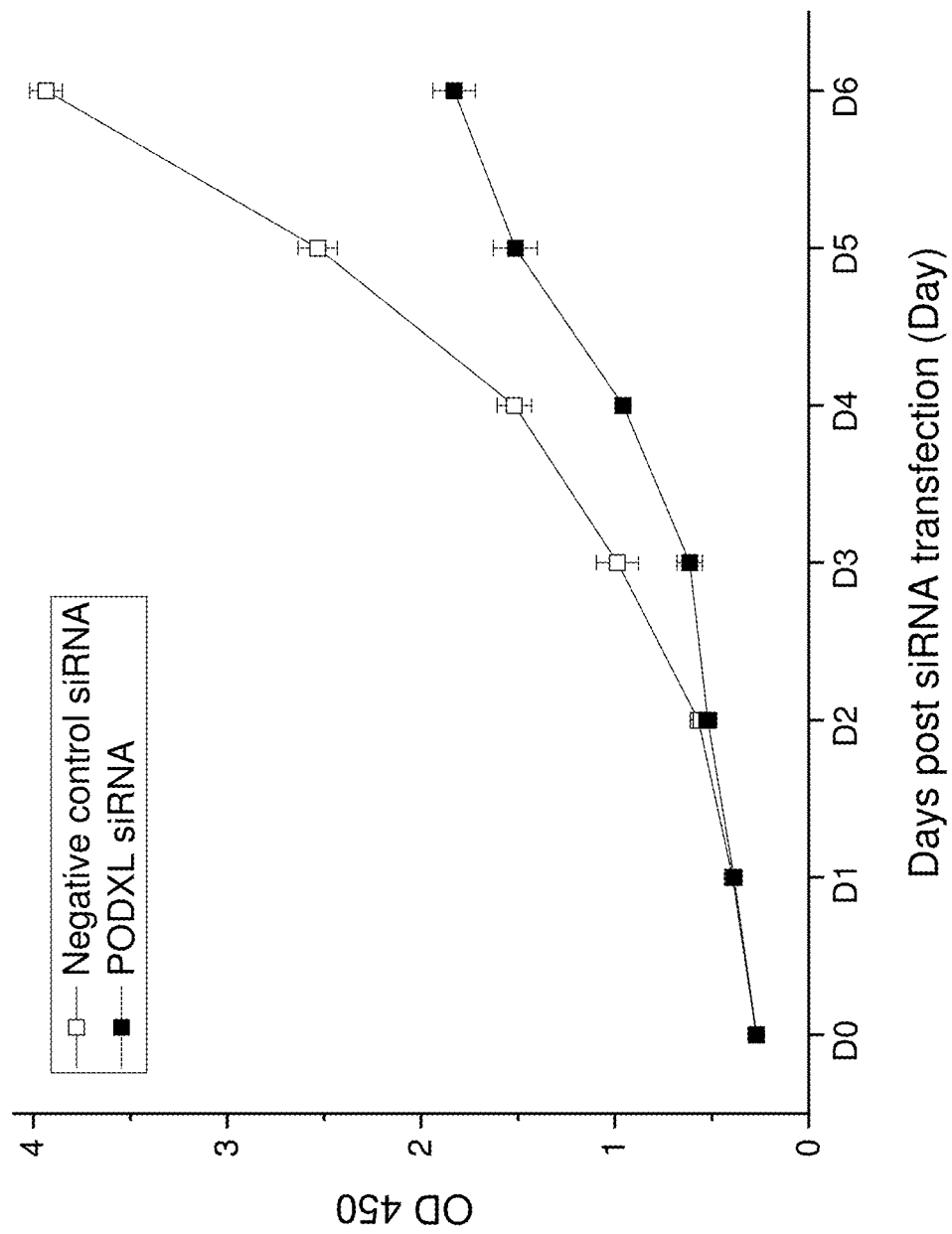

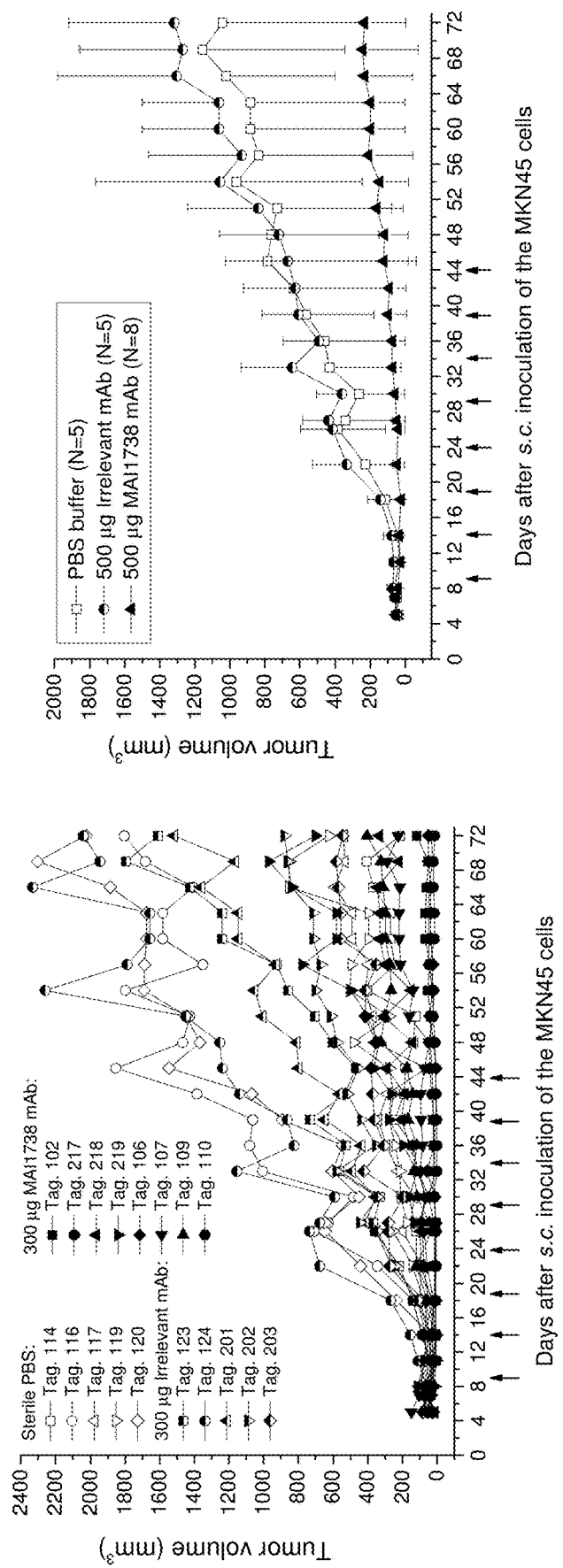

Fig. 10

| Group | Tag # | Tumour colony | Tumor size score | | | | | Average Tumor colonies per mouse | % of tumors per group |
|---|---|---|---|---|---|---|---|---|---|
| | | | 1 | 2 | 3 | 4 | 5 | | |
| PBS treatment (Blank control) | 206 | 4 | 4 | | | | | 2.17 | 100% |
| | 207 | 1 | 1 | | | | | | |
| | 212 | 1 | 1 | | | | | | |
| | 213 | 1 | 0 | 1 | | | | | |
| | 223 | 3 | 2 | | | 1 | | | |
| | 225 | 3 | 2 | 1 | | | | | |
| Irrelevant mAb treatment (Isotype Ab control) | 126 | 3 | 2 | | | | | 1.38 | 87.5% |
| | 222 | 1 | 1 | | | | | | |
| | 127 | 2 | 2 | | | | | | |
| | 128 | 1 | 1 | | | | | | |
| | 211 | 1 | 0 | | | | | | |
| | 209 | 0 | 0 | | | | | | |
| | 210 | 1 | 1 | | | | 1 | | |
| | 216 | 2 | 0 | | | 1 | | | |
| MAI1738 mAb treatment | 1 | 0 | | | | | | 0.1 | 10%* |
| | 133 | 1 | 1 | | | | | | |
| | 129 | 0 | | | | | | | |
| | 130 | 0 | | | | | | | |
| | 131 | 0 | | | | | | | |
| | 132 | 0 | | | | | | | |
| | 135 | 0 | | | | | | | |
| | 136 | 0 | | | | | | | |
| | 220 | 0 | | | | | | | |
| | 221 | 0 | | | | | | | |

* $P < 0.01$

ANTI-PODXL ANTIBODY MAl1738 AND ITS USE FOR CANCER TREATMENT

SEQUENCE LISTING

The instant application contains a Sequence Listing which has been filed electronically in ASCII format and is hereby incorporated by reference in its entirety. Said ASCII copy, created on Nov. 18, 2021, is named MEDAB-APODXL_SL.txt and is 21,655 bytes in size.

FIELD OF THE INVENTION

The present invention relates to the use of antibodies to bind and modulate the activity of podocalyxin-like protein isoform 2 (PODXL-v2) and its variants. The invention also relates to the in vitro, in situ, and/or in vivo diagnosis and/or treatment of mammalian cells or pathological conditions associated with PODXL-v2.

BACKGROUND

Gastric cancer is the fifth most frequently diagnosed cancer that accounts for about 7% of all cancer cases worldwide (over 1,000,000 new cases in 2018) (Bray et al, 2018). It is particularly prevalent in Asian countries such as China, Japan, and South Korea. Although the mortality of gastric cancer significantly decreased significantly in Japan in recent years due to popularity of gastroscopy and surgical intervention, in other countries without access to earlier diagnosis, the mortality remains very high. Currently, gastric cancer is the third most common cause of cancer-related mortality globally (estimated 783,000 deaths in 2018). Despite of striking improvements in surgery and subsequent radiotherapy and chemotherapy, the prognosis for the patients with advanced stage gastric cancer is still poor, especially for those having lymph node metastasis. Use of targeted therapies for gastric cancer, including small molecules and therapeutic antibodies, is limited due to the lack of a highly specific identified target in gastric cancer cells. Although Trastuzumab, an anti-HER2 receptor mAb, and Ramucirumab, an anti-vascular endothelial growth factor receptor-2 (VEGFR-2) mAb, have been approved by FDA to be combined with chemotherapy for the treatment of locally advanced and metastatic gastric cancer, their efficacy is limited (Bang et al, 2010; Wilke et al, 2014; Fuchs et al, 2014). Some therapeutic antibodies for gastric cancer, such as Zolbetuximab against Claudin-18.2 (Sahin et al, 2018), are currently in clinical investigation. Discovery of new biomarkers for gastric cancer that may lead to the development of improved therapeutic strategies.

Therapeutic antibodies have become a widespread treatment for various cancer types due to their specificity, efficacy, safety and reduced adverse events and side effects. When a tumor-specific antigen is targeted, the antibody administered mainly accumulates at the tumor site, attacking the tumor cells as an antagonist, or by mediating complement-dependent cytotoxicity (CDC), antibody-dependent cellular cytotoxicity (ADCC), or antibody-dependent cell phagocytosis (ADCP). Even if a tumor-specific antibody does not have an anti-tumor activity, it can kill cancer cells by conjugation with cytotoxic agents (antibody drug conjugation, ADC) for systemic administration, with radionuclides for localized radiotherapy, or by application in chimeric antigen receptor-modified T cell (CAR-T) immunotherapy.

In an earlier-filed patent application (Patent Number: CN105504060), a mAb designated MS17-38 was found to specifically bind to gastric cancer cells via a cell-surface glycoprotein, podocalyxin-like protein isoform 2 (PODXL-v2), which is a member of the CD34 family of sialomucins. The gene encoding PODXL is located in the 7q32.3 locus and there are two RNA transcript variants which encode two isoforms of protein precursors, PODXL-v1 and PODXL-v2. PODXL-v1 is widely expressed on podocytes, vascular endothelium, mesothelial cells and platelets, as well as in a number of cancer tissues (Nielsen and McNagny, 2009). PODXL-v2 differs from PODXL-v1 by lacking 32 amino acid residues in the extracellular domain and is specifically expressed or up-regulated in numerous cancer cell types as well as in small blood vessels in tumor tissues. Based on patient survival data, high levels of PODXL transcripts or proteins in tumor cells is associated with poor prognosis in multiple human cancer tissues, such as prostate cancer (Casey et al., 2006), glioblastoma (Binder et al., 2013), colorectal cancer (Larsson et al., 2012), breast cancer (Forse et al., 2013; Snyder et al., 2015), urothelial bladder cancer (Boman et al., 2013, 2017), pancreatic cancer (Taniuchi et al., 2016), and others. Consequently, PODXL was proposed as a potential target for therapeutic antibodies in treatment of cancer types that overexpress PODXL-v2.

SUMMARY

A second subclone of the PODXL-v2-specific mAb, designated MAb1738, which differed from MS17-38.1 in the nucleotide sequence of the light chain variable region, was found to have a higher affinity to gastric cancer cells. In vitro and in vivo studies showed that MAb1738 was capable of inducing downstream signaling pathways that inhibited gastric cancer cell growth and tumor metastasis. Both MAb1738 and a PODXL-specific siRNA could reduce the expression level of PODXL-v2 and therefore, are likely to be effective anti-cancer agents, since high expression levels of PODXL-v2 are linked to a negative prognosis for various types of cancers.

The coding sequence of the variable region of the light chain of MAb1738 mAb is shown as SEQ ID NO:1 below with the primer sequences underlined.

```
                                                              (SEQ ID NO: 1)
  1 gatattgtgctaactcagtctccagtcaccctgtctgtgactccaggagatagcgtcagt   60

61 ctttcctgcagggccagccaaagtattaacaacaacctacactggtatcaacaaaaatca  120

121 catgagtctccaaggcttctcatcaagtatgcttcccagtccatctctgggatccccccc  180

181 aggttcagtggcagtcgatcagggacagatttcactctcagtatcaacactgtggagact  240

241 gaagattttggagtttatttctgtcaacagagtaacagttggccgctcacgttcggtgct  300

301 gggaccaagctggagctgaaacgggctgatgctgcaccaactgtatcc              348
```

The translated amino acid sequence in the variable region of the light chain was predicted as SEQ ID NO: 2 below and three antigenic determinant regions (CDRs1 to 3, left to right) are marked with underlines.

(SEQ ID NO: 2)
DIVLTQSPVTLSVTPGDSVSLSCRASQSINNNLHWYQQKSHESPRLLIK

YASQSISGIPPRFSGSRSGTDFTLSINTVETEDFGVYFCQQSNSWPLTF

GAGTKLELKRADAAPTVS

The coding sequence of the variable region of the heavy chain of MAb1738 mAb is shown as SEQ ID NO: 3 below with the primer sequences underlined.

(SEQ ID NO: 3)
```
  1 gaggtgaagctggtggagtctgggggaggcttagtgaagcctggagggtccctgaaagtc   60
 61 tcctgtgcagcctctggattcactttcagtacctataccatgtcttgggttcgccagact  120
121 ccggagaagaggctggagtgggtcgcaaccattagtggtggtgttatttacacctactat  180
181 ccagacagtgtgaagggccgattcaccatctccagagacgatgccaagaacactctgtat  240
241 ctgcaaatgagcagtctgaggtctgaggacacggccttgtattactgtgcaagacactat  300
301 agtaactacgagggccaaggtatggactcctggggtcaaggaacctcagtcaccgtctcc  360
361 tcagccaaaacgacaccccatctgaca                                   388
```

The translated amino acid sequence in the variable region of the heavy chain was predicted as SEQ ID NO: 4 below and three antigenic determinant regions (CDRs1 to 3, left to right) are marked with underlines.

(SEQ ID NO: 4)
EVKLVESGGGLVKPGGSLKVSCAASGFTFSTYTMSWVRQTPEKRLEWVA

TISGGVIYTYYPDSVKGRFTISRDDAKNTLYLQMSSLRSEDTALYYCAR

HYSNYEGQGMDSWGQGTSVTVSSAKTTPPSD

This invention relates to Binding Agents (defined below), including antibodies (defined below) such as monoclonal antibodies and fragments and derivatives thereof, which include one or more light chain CDR regions at least 70% (e.g., 70%, 75%, 80%, 85%, 90%, 95%, 97%, 98%, or 99%) identical to the CDR regions of the PODXL-v2-specific mAb, designated MAI1738; including a light chain variable region at least 70% (e.g., 70%, 75%, 80%, 85%, 90%, 95%, 97%, 98%, or 99%) identical to SEQ ID NO: 2. Optionally, the Binding Agent heavy chain variable region is at least 70% (e.g., 70%, 75%, 80%, 85%, 90%, 95%, 97%, 98%, or 99%) identical to SEQ ID NO: 4. The Binding Agent can include a region like the light chain CDR1 of MAI1738, at least 70% (e.g., 70%, 75%, 80%, 85%, 90%, 95%, 97%, 98%, or 99%) identical to the sequence RASQSINNNLH (SEQ ID NO.: 7). The Binding Agent can include a region like the light chain CDR2 of MAI1738, at least 70% (e.g., 70%, 75%, 80%, 85%, 90%, 95%, 97%, 98%, or 99%) identical to the sequence YASQSIS (SEQ ID NO.: 8). The Binding Agent can include a region like the light chain CDR3 of MAI1738, at least 70% (e.g., 70%, 75%, 80%, 85%, 90%, 95%, 97%, 98%, or 99%) identical to the sequence QQSNSWPLT (SEQ ID NO.: 9).

The present application relates to the treatment of cancers, including cancers overexpressing PODXL-v2 with MAb1738, and Binding Agents related to MAI1738, including Binding Agents derived from or having portions at least 70% (e.g., 70%, 75%, 80%, 85%, 90%, 95%, 97%, 98%, or 99%) identical to one or more of the sequences of the light chain CDRs of MAb1738. MAb1738 binds specifically to both PODXL-v2 and PODXL-v2-Del mutant proteins with high affinity, and neutralizes the activity of these proteins.

The Binding Agents of the invention include MAb1738-like or MAb1738-derived antibodies or, an antibody-derived or modified CAR-T, including single-chain variable fragments (scFv) fused to intracellular signaling domains, e.g., the zeta chain of CD3 (CD3ζ). CAR-T is preferably expressed in CAR immune effector cell including T cells and NK cells.

The term Binding Agent(s) includes an antibody (both are interchangeably used in plural form) which is an immunoglobulin molecule capable of binding to a target antigen, such as an antigen on gastric cancer cells, through at least one antigen recognition site, located in the variable region of the immunoglobulin molecule. As used herein, the term "antibody" encompasses not only intact (i.e., full-length) polyclonal or monoclonal antibodies, but also antigen-binding fragments thereof (such as Fab, Fab', F(ab')2, Facb, Fv, Fd), single chain (scFv) or sc(Fv)$_2$, mutants thereof, fusion proteins comprising an antibody portion, humanized antibodies, chimeric antibodies, diabodies, linear antibodies, multispecific antibodies (e.g., bispecific antibodies), single domain antigen binding (SDAB) molecules, a VH or VL domain, or a VHH domain, and any other modified configuration of the immunoglobulin molecule that comprises an antigen recognition site of the required specificity, including glycosylation variants of antibodies, amino acid sequence variants of antibodies, and covalently modified antibodies. Also included are antibody-drug conjugates.

An antibody includes antibodies of any class, such as IgD, IgE, IgG, IgA, or IgM (or a sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2.

The Binding Agents are preferentially used in treating tumor-related diseases including cancers e.g., gliobastoma, prostate cancer, urothelial bladder cancer, esophageal cancer, colorectal cancer, pancreatic cancer, ovarian cancer, liver cancer, gastric cancers and tumor metastasis, including squamous cell carcinoma of the stomach, gastric adenocarcinoma, small cell carcinoma of the stomach, gastric squamous cell carcinoma, gastric carcinoid tumors, and stomach and duodenal cancers.

The appropriate dosage range and dosing regimens can be extrapolated from the in vivo and in vitro experimental results, set forth herein. The Binding Agents are preferentially delivered in a pharmaceutical formulation for therapy; and they can also be used in diagnosis, purification or screening for selection of other Binding Agents.

BRIEF DESCRIPTION OF THE DRAWINGS

FIGS. 2A to 2E (SEQ ID Nos.: 10-12) compare the differences in the cDNA coding sequences for the extracellular domains of the podxl-v2-Del, podxl-v2, and podxl-v1 cDNA. Sequence alignment was generated with the CLUSTAL 0 (1.2.4) program. The point mutations in podxl-v2-Del are indicated in bold with the codon underlined. The deletions are indicated with "–". Identical nucleotides among all three sequences are indicated with * below the alignment. The middle portions of the identical sequences are omitted.

FIG. 6 shows dose-dependent inhibition of cell proliferation of the MKN45 and BGC823 cells upon treatment with MAb1738 mAb in CCK-8 assays. Cells were treated with 8, 30 and 120 μg/mL of MAb1738 mAb or an irrelevant mAb, respectively, at Day 0 and Day 4 as indicated with arrows. Cell survival was monitored by measuring the absorbance at 450 nm two hours after addition of CCK-8 solution for eight or nine days. The Y axis represent the percentage of surviving cells at each time point relative to the live cells on Day 0 (which was designated as 100%) in the same treatment group. Data represent mean±standard deviation (SD) of three independent experiments.

FIGS. 7A and 7B shows MAb1738 inhibited migration of BGC823 cells in transwell migration assays. FIG. 7A illustrates the migration of cells in different wells with or without treatment with MAb1738 or the control mAb in a colorimetric cell migration assay. Trypan blue was used to stain the cells treated with PBS (blank control), 5 μg/mL irrelevant mAb (isotype control), or 5 μg/mL MAI1738 on Day 3. The columns represent mean±SD of three wells in the same treatment group. Relative percentage of cells migrating are labeled on top of the columns. There was a significant difference between the MAI1738-treatment group and the other two control groups (P<0.05).

FIG. 7B shows images of the transwell assays revealing the difference in migration capability of the BGC823 cells treated with MAb1738 or the irrelevant mAb.

FIGS. 8A to 8C show the podxl-v2-specific siRNA inhibited the migration and proliferation of the MKN45 cells.

FIG. 8A is the images of a transwell assay showing the difference in migration capability between the MKN45 cells transfected with podxl-v2 siRNA and those that were transfected with a negative control siRNA.

FIG. 8B is a comparison of MKN45 cell numbers migrating through transwell inserts, between the podxl-v2 siRNA-treated samples with the negative control siRNA-treated samples. Data represent mean±SD of triplicate samples.

FIG. 8C shows introduction of podxl-v2 siRNA into the MKN45 cells significantly inhibited cell proliferation in the CCK-8 assays (P<0.05).

FIGS. 9A to 9C show the results demonstrating MAb1738 inhibited the growth of GC tumor in an in vivo xenograft nu/nu mouse tumor model.

FIG. 9A: Comparison of tumor volumes in an MKN45 xenograft tumor model treated with low dose (150 μg/mouse) of MAb1738 (treatment group) or an irrelevant mAb (isotype control group). All the tumors were harvested on the 30th day after subcutaneous (s.c.) inoculation of the MKN45 cells. The left panel shows the tumor volume of individual mice and the right panel shows the average tumor volume±SD in the same group. Arrows indicate the days of mAb treatments. The average tumor volumes between these two groups were significantly different (P<0.05).

FIG. 9B shows comparison of tumor volumes in the MKN45 xenograft tumor model treated with high dose (300 μg/mouse) of MAb1738 (treatment group) or the irrelevant mAb (isotope control group), or equal volume of phosphate buffered saline (PBS, blank control group). All the tumors were harvested 72 days after s.c. inoculation of the MKN45 cells. The left panel shows the tumor volume of individual mice and the right panel shows the average tumor volume±SD in the same group. Arrows indicate the days of mAb treatments. The average volume of the tumors in the treatment group was significantly lower than those of the two control groups and the difference became more evident over time (P<0.01). Data represent means±SD of all the tumor volumes in the same group.

FIG. 9C shows representative images of the tumors of the high-dose experiment. Difference in the sizes of the tumors between the treatment group and the control groups is evident.

FIG. 10 shows MAb1738 prevented lung metastasis of GC cells in a xenograft nu/nu mouse tumor model. The number of tumor colonies in the lungs formed 65 days after i.v. injection of the MKN45 cells and the size score of each tumor colony are listed. Nine out of ten mice (90%) in the MAI1738-treatment group did not have lung metastasis, whereas all (5/5) or 87.5% (7/8) in the control groups had metastatic colonies in the lungs. The difference was statistically significant (P<0.01).

DETAILED DESCRIPTION

Figure 1A:
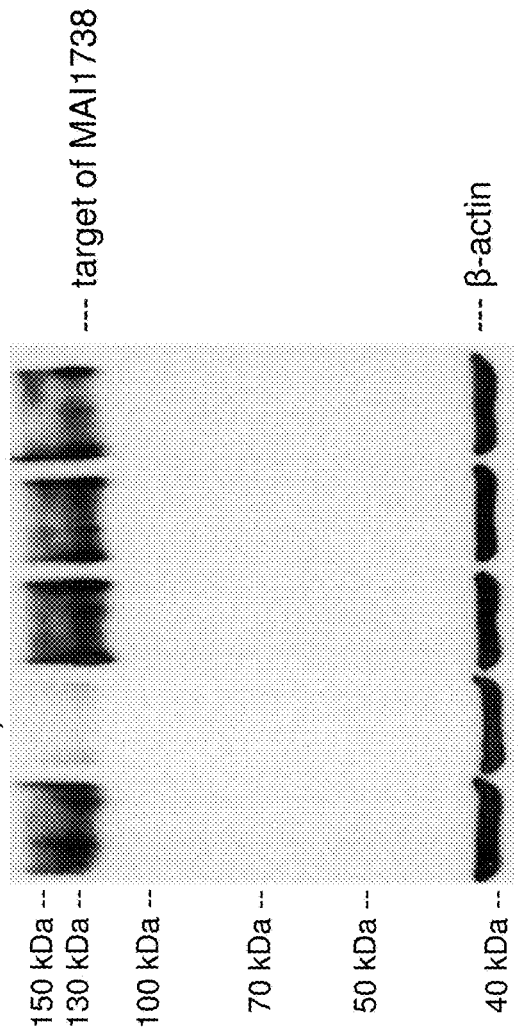
FIG. 1A shows that MAb1738 interacts with PODXL-v2 expressed on the cell surface of MKN45 cells in a Western blot analysis. The MKN45 cell lysate (Lane 2), following treatment with the podxl-v2-specific siRNA, but not other siRNAs, presented no target protein for MAil1738. β-actin was detected as a sample loading control. MAb1738 and a mouse anti-β-actin mAb were simultaneously used to probe the PVDF membrane. An HRP-conjugated anti-mouse IgG-Fc pAb was used as the secondary antibody. FAM120B: Constitutive co-activator of peroxisome proliferator-activated receptor gamma; PODXL-v2: Podocalyxin-like protein isoform 2 precursor; Sec16A: Protein transport protein Sec16A; SMARCC1: SWI/SNF complex subunit.

It should be understood that unless the context clearly dictates otherwise, the singular forms "a", "an" and "the" include plural forms. Monoclonal antibodies are referred to sometimes as "mAbs." The terms "Binding Agent" and "antibody," singular and plural forms, are used interchangeably.

Antibodies described herein can be murine, rat, human, or any other origin (including chimeric or humanized antibodies, including as described in U.S. Pat. No. 7,317,091B2, and including such antibodies generated by affinity maturation). In some examples, the antibody comprises a modified constant region, such as a constant region that is immunologically inert, e.g., does not trigger complement mediated lysis, or does not stimulate antibody-dependent cell mediated cytotoxicity (ADCC). ADCC activity can be assessed using methods disclosed in U.S. Pat. No. 5,500,362.

Humanized antibodies refer to forms of non-human (e.g. murine) antibodies that are specific chimeric immunoglobulins, immunoglobulin chains, or antigen-binding fragments thereof that contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, six) which are altered with respect to the original antibody. Humanized antibodies may also involve affinity maturation. See Jones et al., Nature, 321:522-525 (1986); Riechmann et al., Nature, 332:323-327 (1988); Verhoeyen et al., Science, 239: 1534-1536 (1988).

In another example, the antibody described herein is a chimeric antibody, which can include a heavy constant region and a light constant region from a human antibody. See, e.g., Morrison et al. (1984) Proc. Natl. Acad. Sci. USA 81, 6851; Neuberger et al. (1984) Nature 312, 604; and Takeda et al. (1984) Nature 314:452. Chimeric antibodies refer to antibodies having a variable region or part of variable region from a first species and a constant region from a second species. Typically, in these chimeric antibodies, the variable region of both light and heavy chains mimics the variable regions of antibodies derived from one species of mammals (e.g., a non-human mammal such as mouse, rabbit, and rat), while the constant portions are homologous to the sequences in antibodies derived from another mammal such as human. In some embodiments, amino acid modifications can be made in the variable region and/or the constant region. See U.S. Pat. No. 4,816,567.

The "percent identity" of two amino acid sequences can be determined arithmetically, by counting and comparing, for the shorter sequences described or claimed herein, or by using the algorithm of Karlin and Altschul Proc. Natl. Acad. Set USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, word-length=3 to obtain amino acid sequences homologous to the protein molecules of interest. Where gaps exist between two sequences, Gapped BLAST can be utilized as described in Altschul et al, Nucleic Acids Res. 25(17):3389-3402, 1997. When utilizing BLAST and Gapped BLAST programs, the default parameters of the respective programs (e.g., XBLAST and NBLAST) can be used.

Making Binding Agents

A number of methodologies have been developed to prepare chimeric, humanized or human antibodies for human in vivo therapeutic applications. The most used methodology is to prepare mouse mAbs using hybridoma methodology and then to humanize the mAbs by converting the framework regions of the VH and VL domains and constant domains of the mAbs into homologous human framework regions of human VH and VL domains and constant regions of a desirable human y immunoglobulin isotype and subclass. See U.S. Pat. No. 5,225,539.

Monoclonal antibodies can be made by the conventional hybridoma technology. Kohler et al., Nature, 256:495 (1975). In the hybridoma method, a mouse or other appropriate host animal, such as a hamster or rabbit, is immunized as hereinabove described to elicit lymphocytes that produce or are capable of producing antibodies that will specifically bind to the protein used for immunization. Alternatively, lymphocytes may be immunized in vitro.

To prepare monoclonal antibodies, immune cells are collected from the mammal immunized with the antigen and checked for the increased level of desired antibodies in the serum as described above, and are subjected to cell fusion. The immune cells used for cell fusion are preferably obtained from spleen. Other preferred parental cells to be fused with the above immunocyte include, for example, myeloma cells of mammalians, and more preferably myeloma cells having an acquired property for the selection of fused cells by drugs.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 cells available from the American Type Culture Collection, Rockville, Md. USA. Human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, pp. 51-63 (Marcel Dekker, Inc., New York, 1987)).

The above immunocyte and myeloma cells can be fused according to known methods, for example, the method of Milstein et al. (Galfre et al., Methods Enzymol. 73:3-46, 1981). Lymphocytes are fused with myeloma cells using a suitable fusing agent, such as polyethylene glycol, to form a hybridoma cell (Goding, Monoclonal Antibodies: Principles and Practice, pp. 59-103 (Academic Press, 1986)). Resulting hybridomas obtained by the cell fusion may be selected by cultivating them in a standard selection medium, such as HAT medium (hypoxanthine, aminopterin, and thymidine containing medium). The cell culture is typically continued in the HAT medium for several days to several weeks, the time being sufficient to allow all the other cells, with the exception of the desired hybridoma (non-fused cells), to die. Then, the standard limiting dilution is performed to screen and clone a hybridoma cell producing the desired antibody.

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells. Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay. Measurement of absorbance in enzyme-linked immunosorbent assay (ELISA), enzyme immunoassay (EIA), radioimmunoassay (RIA), and/or immunofluorescence may be used to measure the antigen binding activity of the antibody.

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography. In addition, the hybridoma cells may be grown in vivo as ascites tumors in an animal; e.g., in the abdominal cavity of a mouse.

The obtained monoclonal antibodies can be purified by, for example, ammonium sulfate precipitation, a protein A or protein G column, DEAE ion exchange chromatography, or an affinity column to which the protein of the present invention is coupled. The antibody of the present invention can be used for purification and detection of gastric cancer cells.

The monoclonal antibodies thus obtained can be also recombinantly prepared using genetic engineering techniques (see, for example, Borrebaeck C. A. K. and Larrick J. W. Therapeutic Monoclonal Antibodies, published in the United Kingdom by MacMillan Publishers LTD, 1990). A DNA encoding an antibody may be cloned from an immune cell, such as a hybridoma or an immunized lymphocyte producing the antibody, inserted into an appropriate vector, and introduced into host cells to prepare a recombinant antibody. Recombinant techniques are described in the literature, particularly in Sambrook et al., MOLECULAR CLONING: A LABORATORY MANUAL, Second edition, Cold Spring Harbor Laboratory Press, 1989, and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; and Kontermann and Dübel, ANTIBODY ENGINEERING, Springer Lab manual, Springer-Verlag Berlin Heidelberg, 2001) and the like.

When the obtained antibody is to be administered to humans in treatment, a human antibody or a humanized antibody is preferable for reducing immunogenicity. For example, transgenic animals having a repertory of human antibody genes may be immunized with an antigen selected from human gastric cancer cell proteins, or their lysates. Antibody producing cells are then collected from the animals and fused with myeloma cells to obtain hybridomas, from which human antibodies against the antigen can be prepared. Alternatively, an immune cell, such as an immunized lymphocyte, producing antibodies may be immortalized by an oncogene and used for preparing monoclonal antibodies.

DNA encoding the monoclonal antibodies can be readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as E. coli cells, simian COS cells, Chinese hamster ovary (CHO) cells, or myeloma cells that do not otherwise produce immunoglobulin protein, to produce monoclonal antibodies in the recombinant host cells. Review articles on recombinant expression in bacteria of DNA encoding the antibody include Skerra et al., Curr. Opinion in Immunol., 5:256-262 (1993) and Pluckthun, Immunol. Rev., 130: 151-188 (1992). DNAs encoding the antibodies produced by the hybridoma cells described above can be genetically modified, via routine technology, to produce genetically engineered antibodies. Genetically engineered antibodies, such as humanized antibodies, chimeric antibodies, single-chain antibodies, diabodies, bi-specific antibodies and multi-specific antibodies, can be produced via, e.g., conventional recombinant technology. The DNA can then be modified, for example, by substituting the coding sequence for human heavy and light chain constant domains in place of the homologous murine sequences, Morrison et al., (1984) Proc. Nat. Acad. Sci. 81:6851, or by covalently joining to the immunoglobulin coding sequence all or part of the coding sequence for a non-immunoglobulin polypeptide. In that manner, genetically engineered antibodies, including chimeric or humanized antibodies can be prepared that have the binding specificity of a target antigen.

Alternatively, certain transgenic animals (e.g., mice) are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-258

(1993); Bruggermann et al., Year in Immuno., 7:33 (1993). See also the Xenomouse from Amgen, Inc. (Fremont, Calif.) and HuMAb-Mouse R™ and TC Mouse™ from Medarex, Inc. (Princeton, N.J.). In another alternative, antibodies may be made recombinantly by phage display technology. See, for example, U.S. Pat. Nos. 5,565,332; 5,580,717; 5,733,743; and 6,265,150; and Winter et al., (1994) Annu. Rev. Immunol. 12:433-455; (Hoogenboom et al., J. Mol. Biol., 227:381 (1991); Marks et al., J. Mol. Biol., 222:581-597 (1991)). Alternatively, the phage display technology (Mc-Cafferty et al., (1990) Nature 348:552-553) can be used to produce human antibodies and antibody fragments in vitro, from immunoglobulin variable (V) domain gene repertoires from unimmunized donors.

F(ab')$_2$ fragments can be produced by pepsin digestion or other proteolytic digestion of intact antibodies (see, e.g., Morimoto et al., Journal of Biochemical and Biophysical Methods 24: 107-117 (1992) and Brennan et al., Science 229: 81 (1985)). Fab fragments that can be generated by reducing the disulfide bridges of F(ab')$_2$ fragments. Such fragments can now also be produced directly by recombinant host cells. For example, the antibody fragments can be isolated from an antibody phage library. Alternatively, F(ab')$_2$-SH fragments can be directly recovered from E. coli and chemically coupled to form F(ab')$_2$ fragments (Carter et al., Bio/Technology 10: 163-167 (1992)). According to another approach, F(ab') 2 fragments can be isolated directly from recombinant host cell culture.

U.S. Pat. No. 5,932,448, discloses making of bispecific antibodies with Fab' portions joined by a leucine zipper; U.S. Pat. No. 7,538,196, discloses making of bispecific antibodies where portions are joined with a linker; U.S. Pat. No. 8,148,496 discloses a multi-specific Fv antibody construct having at least four variable domains which are linked with each other via peptide linkers.

US Publ'n No. 20170335281 describes making of a genetically modified T cell expressing a CAR that comprises an antigen binding domain that binds to a cancer associated antigen. The same general techniques can be applied to modify T cells or other immune effector cells to express one or more of CDR1, CDR2 and CDR3 of MAI1738, as the antigen binding domain, for cancer treatment. The antigen binding domain of the CAR polypeptide molecule can include any antibody, antibody fragment, an scFv, a Fv, a Fab, a (Fab')2, a single domain antibody (SDAB), a VH or VL domain, or a VHH domain.

SDAB molecules are disclosed in WO 9404678 and Hamers-Casterman, C. et al. (1993) Nature 363:446-448. SDAB molecule is a naturally occurring single domain antigen binding molecule known as heavy chain devoid of light chains. In one type of SDAB, the variable domain is derived from a heavy chain molecule naturally devoid of light chain is can be derived from Camelidae species, for example in camel, llama, dromedary, alpaca and guanaco. Other species besides Camelidae may also produce heavy chain molecules naturally devoid of light chain. The SDAB molecules can be recombinant, CDR-grafted, humanized, camelized, de-immunized and/or in vitro generated (e.g., selected by phage display).

Any of the Binding Agents above can be used in an antibody-drug conjugate, which targets to cancer cells, by linking it to a cytotoxin for the cancerous cells. See U.S. Pat. No. 9,764,041; US Publ'n No. 20170151343.

High Affinity Antibody Variants

Antibodies with variations of the sequences set forth herein are within the scope of the invention. One type of variant is a high affinity variant, as set forth below.

Antibodies should be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved.

Examples of framework region residues to modify include those which non-covalently bind target directly (Amit et al. Science 233: 747-753 (1986)); interact with/effect the conformation of CDR (Chothia et al. J. Mol. Biol. 196: 901-917 (1987)); and/or participate in the VL-VH interface (EP 239 400 B1). In certain embodiments, modification of one or more of such framework region residues results in an enhancement of the binding affinity of the antibody for the target of interest.

Nucleic acid molecules encoding amino acid sequence variants are prepared by a variety of methods known in the art. These methods include, but are not limited to, oligonucleotide-mediated (or site-directed) mutagenesis, PCR mutagenesis, and cassette mutagenesis of an earlier prepared variant or a non-variant version of the species-dependent antibody. The preferred method for generating variants is an oligonucleotide-mediated synthesis. In certain embodiments, the antibody variant will only have a single hypervariable region residue substituted, e.g. from about two to about fifteen hypervariable region substitutions.

One method for generating the library of variants is by oligonucleotide mediated synthesis. Three oligonucleotides of approximately 100 nucleotides each may be synthesized spanning the entire light chain or heavy chain variable region. Each oligonucleotide may comprise: (1) a 60 amino acid stretch generated by the triplet (NNK).sub.20 where N is any nucleotide and K is G or T (SEQ ID NO: 16), and (2) an approximately 15-30 nucleotide overlap with either the next oligo or with the vector sequence at each end. Upon annealing of these three oligonucleotides in a PCR reaction, the polymerase will fill in the opposite strand generating a complete double stranded heavy chain or light chain variable region sequence. The number of triplets may be adjusted to any length of repeats and their position within the oligonucleotide may be chosen so as to only substitute amino acids in a given CDR or framework region. By using (NNK), all twenty amino acids are possible at each position in the encoded variants. The overlapping sequence of 5-10 amino acids (15-30 nucleotides) will not be substituted, but this may be chosen to fall within the stacking regions of the framework, or may substituted by a separate or subsequent round of synthesis. Methods for synthesizing oligonucleotides are well known in the art and are also commercially available. Methods for generating the antibody variants from these oligonucleotides are also well known in the art, e.g., PCR.

The library of heavy and light chain variants, differing at random positions in their sequence, can be constructed in any expression vector, such as a bacteriophage, each of which contains DNA encoding a particular heavy and light chain variant.

Following production of the antibody variants, the biological activity of variant relative to the parent antibody is determined. As noted above, this involves determining the binding affinity of the variant for the target. Numerous high-throughput methods exist for rapidly screen antibody variants for their ability to bind the target of interest.

One or more of the antibody variants selected from this initial screen may then be screened for enhanced binding affinity relative to the parent antibody. One common method for determining binding affinity is by assessing the association and dissociation rate constants using a BIAcore surface plasmon resonance system (BIAcore, Inc., now GE Healthcare). A biosensor chip is activated for covalent coupling of the target according to the manufacturer's (BIAcore) instructions. The target is then diluted and injected over the chip to obtain a signal in response units (RU) of immobilized material. Since the signal in RU is proportional to the mass of immobilized material, this represents a range of immobilized target densities on the matrix. Dissociation data are fit to a one-site model to obtain Koff+/−s.d. (standard deviation of measurements). Pseudo-first order rate constant (Ks) are calculated for each association curve, and plotted as a function of protein concentration to obtain Kon+/−s.e. (standard error of fit). Equilibrium dissociation constants for binding, Kd's, are calculated from SPR measurements as Koff/kon. Since the equilibrium dissociation constant, Kd, is inversely proportional to Koff, an estimate of affinity improvement can be made assuming the association rate (Kon) is a constant for all variants.

The resulting candidate(s) with high affinity may optionally be subjected to one or more further biological activity assays to confirm that the antibody variant(s) with enhanced binding affinity still retain the desired therapeutic attributes, as can be tested in the assays described in the examples below. The optimal antibody variant retains the ability to bind the target with a binding affinity significantly higher than the parent antibody.

The antibody variant(s) so selected may be subjected to further modifications oftentimes depending upon the intended use of the antibody. Such modifications may involve further alteration of the amino acid sequence, fusion to heterologous polypeptide(s) and/or covalent modifications such as those elaborated below. For example, any cysteine residues not involved in maintaining the proper conformation of the antibody variant may be substituted, generally with serine, to improve the oxidative stability of the molecule and prevent aberrant cross linking. Conversely, (a) cysteine bond(s) may be added to the antibody to improve its stability (particularly where the antibody is an antibody fragment such as an Fv fragment).

Formulations

After preparation of a suitable antibody, it can be prepared in a formulation for administration to a subject. A lyophilized formulation is preferred, which as a first step, requires preparing a pre-lyophilized formulation. The amount of antibody in the pre-lyophilized formulation is determined taking into account the desired dose volumes, mode(s) of administration etc. The protein is generally present in solution. For example, the protein may be present in a pH-buffered solution at a pH from o about 4-8, and preferably from about 5-7. Exemplary buffers include histidine, phosphate, Tris, citrate, succinate and other organic acids. The buffer concentration can be from about 1 mM to about 20 mM, or from about 3 mM to about 15 mM, depending, for example, on the buffer and the desired isotonicity of the formulation (e.g. of the reconstituted formulation). The preferred buffer is histidine as it can have lyoprotective properties. Succinate is also a useful buffer.

The lyoprotectant is added to the pre-lyophilized formulation. In preferred embodiments, the lyoprotectant is a non-reducing sugar such as sucrose or trehalose. The amount of lyoprotectant in the pre-lyophilized formulation is generally such that, upon reconstitution, the resulting formulation will be isotonic, as preferred, though hypertonic reconstituted formulations may also be suitable. In addition, the amount of lyoprotectant must not be too low such that an unacceptable amount of degradation/aggregation of the protein occurs upon lyophilization.

Where the lyoprotectant is a sugar (such as sucrose or trehalose) and the protein is an antibody, exemplary lyoprotectant concentrations in the pre-lyophilized formulation are from about 10 mM to about 400 mM, and preferably from about 30 mM to 5 about 300 mM, and most preferably from about 50 mM to about 100 mM.

The ratio of protein to lyoprotectant is selected for each protein and lyoprotectant combination. In the case of an antibody as the protein of choice and a sugar (e.g., sucrose or trehalose) as the lyoprotectant for generating an isotonic reconstituted formulation with a high protein concentration, the molar ratio of lyoprotectant to antibody may be from about 100 to about 1500 moles lyoprotectant to 1 mole antibody, and preferably from about 200 to about 1000 moles of lyoprotectant to 1 mole antibody, including from about 200 to about 600 moles of lyoprotectant to 1 mole antibody.

In preferred embodiments, it has been found to be desirable to add a surfactant to the pre-lyophilized formulation. Alternatively, or in addition, the surfactant may be added to the lyophilized formulation and/or the reconstituted formulation. Exemplary surfactants include nonionic surfactants such as polysorbates (e.g. polysorbates 20 or 80); poloxamers (e.g. poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palnidopropyl-, or isostearamidopropyl-betaine (e.g lauroamidopropyl); myristamidopropyl-, palmidopropyl-, or isostearamidopropyl-dimethylamine; sodium methyl cocoyl-, or disodium methyl oleyl-taurate; and the MONAQUAT™ series (Mona Industries, Inc., Paterson, N.J.), polyethyl glycol, polypropyl glycol, and copolymers of ethylene and propylene glycol (e.g. Pluronics, PF68 etc). The amount of surfactant added is such that it reduces aggregation of the reconstituted protein and minimizes the formation of particulates after reconstitution. For example, the surfactant may be present in the pre-lyophilized formulation in an amount from about 0.001-0.5%, and preferably from about 0.005-0.05%.

A mixture of the lyoprotectant (such as sucrose or trehalose) and a bulking agent (e.g. mannitol or glycine) may be used in the preparation of the pre-lyophilization formulation. The bulking agent may allow for the production of a uniform lyophilized cake without excessive pockets therein.

Other pharmaceutically acceptable carriers, excipients or stabilizers such as those described in Remington's Pharmaceutical Sciences 16th edition, Osol, A. Ed. (1980) may be included in the pre-lyophilized formulation (and/or the lyophilized formulation and/or the reconstituted formulation) provided that they do not adversely affect the desired characteristics of the formulation. Acceptable carriers, excipients or stabilizers are nontoxic to recipients at the dosages and concentrations employed and include; additional buffering agents; preservatives; co-solvents; antioxidants including ascorbic acid and methionine; chelating agents such as EDTA; metal complexes (e.g. Zn-protein complexes); biodegradable polymers such as polyesters; and/or salt-forming counterions such as sodium.

The pharmaceutical compositions and formulations described herein are preferably stable, so as to retain its physical and chemical stability and integrity upon storage. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993). Stability can be measured at a selected temperature for a selected time period.

The formulations to be used for in vivo administration must be sterile. This is readily accomplished by filtration through sterile filtration membranes, prior to, or following, lyophilization and reconstitution. Alternatively, sterility of the entire mixture may be accomplished by autoclaving the ingredients, except for protein, at about 120° C. for about 30 minutes.

After the protein, lyoprotectant and other optional components are mixed together, the formulation is lyophilized. Many different freeze-dryers are available for this purpose such as Hull50® (Hull, USA) or GT20® (Leybold-Heraeus, Germany) freeze-dryers. Freeze-drying is accomplished by freezing the formulation and subsequently subliming ice from the frozen content at a temperature suitable for primary drying. Under this condition, the product temperature is below the eutectic point or the collapse temperature of the formulation.

Typically, the shelf temperature for the primary drying will range from about −30 to 25° C. (provided the product remains frozen during primary drying) at a suitable pressure, ranging typically from about 50 to 250 mTorr. The formulation, size and type of the container holding the sample (e.g., glass vial) and the volume of liquid will mainly dictate the time required for drying, which can range from a few hours to several days (e.g. 40-60 hours). A secondary drying stage may be carried out at about 0-40° C., depending primarily on the type and size of container and the type of protein employed. For example, the shelf temperature throughout the entire water removal phase of lyophilization may be from about 15-30° C. (e.g., about 20° C.). The time and pressure required for secondary drying will be that which produces a suitable lyophilized cake, dependent, e.g., on the temperature and other parameters. The secondary drying time is dictated by the desired residual moisture level in the product and typically takes at least about 5 hours (e.g. 10-15 hours). The pressure may be the same as that employed during the primary drying step. Freeze-drying conditions can be varied depending on the formulation and vial size.

In some instances, it may be desirable to lyophilize the protein formulation in the container in which reconstitution of the protein is to be carried out in order to avoid a transfer step. The container in this instance may, for example, be a 3, 5, 10, 20, 50 or 100 cc vial. As a general proposition, lyophilization will result in a lyophilized formulation in which the moisture content thereof is less than about 5%, and preferably less than about 3%.

At the desired stage, typically when it is time to administer the protein to the patient, the lyophilized formulation may be reconstituted with a diluent such that the protein concentration in the reconstituted formulation is preferably similar to that of the pre-lyophilized formulation.

Reconstitution generally takes place at a temperature of about 25° C. to ensure complete hydration, although other temperatures may be employed as desired. The time required for reconstitution will depend, e.g., on the type of diluent, amount of excipient(s) and protein. Exemplary diluents include sterile water, bacteriostatic water for injection (BWFI), a pH buffered solution (e.g. phosphate-buffered saline), sterile saline solution, Ringer's solution or dextrose solution. The diluent optionally contains a preservative. Exemplary preservatives have been described above, with aromatic alcohols such as benzyl or phenol alcohol being the preferred preservatives. The amount of preservative employed is determined by assessing different preservative concentrations for compatibility with the protein and preservative efficacy testing. For example, if the preservative is an aromatic alcohol (such as benzyl alcohol), it can be present in an amount from about 0.1-2.0% and preferably from about 0.5-1.5%, but most preferably about 1.0-1.2%.

Alternatively, a non-lyophilized formulation may be used, including a Binding Agent and any of the well-known carriers, excipients, buffers, stabilizers, preservatives, adjuvants and other additives described herein and well known in the art.

Dosages and Administration

The formulation described above can be administered to a subject (e.g., a human) in need of the treatment via a suitable route, such as administration by intravenous, intramuscular, intraperitoneal, intracerebrospinal, subcutaneous, intracutaneous, intraarticular, intrasynovial, intrathecal, intradermal, intratumoral, intranodal, intramedulla, oral, inhalation or topical routes; or it may be administered orally, by inhalation spray, topically, rectally, nasally, buccally, vaginally or via an implanted reservoir; and in any case, as a bolus or by continuous infusion over a period of time; or via injectable depot routes of administration such as using 1-, 3-, or 6-month depot injectable or biodegradable materials and methods.

Commercially available nebulizers for liquid formulations, including jet nebulizers and ultrasonic nebulizers are useful for administration. Liquid formulations can be directly nebulized and lyophilized powder can be nebulized after reconstitution. Alternatively, antibodies can be aerosolized using a fluorocarbon formulation and a metered dose inhaler, or inhaled as a lyophilized and milled powder. Where CAR is deployed in the invention, compositions of immune effector cells (e.g., T cells, NK cells) may be injected directly into a tumor, lymph node, or site of infection, or elsewhere.

The subject to be treated by the methods described herein can be a mammal, more preferably a human. Mammals include, but are not limited to, farm animals, sport animals, pets, primates, horses, dogs, cats, mice and rats.

An "effective amount" refers to the amount of active agent required to confer therapeutic effect on the subject, either alone or in combination with one or more other active agents. Effective amounts vary, depending on the particular condition being treated, the severity of the condition, the individual patient parameters including age, physical condition, size, gender and weight, the duration of the treatment, the nature of concurrent therapy (if any), the specific route of administration and like factors, all of which are well known to those of ordinary skill in the art and can be addressed with no more than routine experimentation. It is generally preferred that a maximum dose of the individual components or combinations thereof be used, that is, the highest safe dose according to sound medical judgment. A lower dose or tolerable dose for medical reasons, psychological reasons or other reasons, is also appropriate.

Empirical considerations, such as the antibody half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of the gastric cancer. Alternatively, sustained continuous release formulations of antibody may be appropriate. Various formulations and devices for achieving sustained release are known in the art.

In one example, dosages for an antibody as described herein may be determined empirically in individuals who have been given one or more administration(s) of the antibody. Individuals are given incremental dosages of the antibody. To assess efficacy of the antibody, an indicator of the disease (e.g., tumor growth) can be followed according to routine practice.

Generally, for administration of any of the antibodies described herein, an initial candidate dosage can be extrapolated from the experiments described below. For repeated administrations over several days or longer, depending on the condition, the treatment is sustained until a desired suppression of symptoms occurs or until sufficient therapeutic levels are achieved to alleviate the cancer. An exemplary dosing regimen comprises administering an initial higher dose, followed by a lower maintenance dose. However, other dosage regimens may be useful, depending on the pattern of pharmacokinetic decay that the practitioner wishes to achieve. For example, dosing from one-four times a week is contemplated. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the antibody used) can vary over time.

Conventional methods, known to those of ordinary skill in the art of medicine, can be used to administer the pharmaceutical composition to the subject, depending upon the treatment goal and the cancer site.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like).

For intravenous injection, water soluble antibodies can be administered by the drip method, whereby a pharmaceutical formulation containing the antibody and a physiologically acceptable excipients is infused. Physiologically acceptable excipients may include, for example, 5% dextrose, 0.9% saline, Ringer's solution or other suitable excipients.

Intramuscular preparations, e.g., a sterile formulation of a suitable soluble salt form of the antibody, can be dissolved and administered in a pharmaceutical excipient such as Water-for-Injection, 0.9% saline, or 5% glucose solution.

In one embodiment, an antibody is administered via site-specific or targeted local delivery techniques. Examples of site-specific or targeted local delivery techniques include various implantable depot sources of the antibody or local delivery catheters, such as infusion catheters, an indwelling catheter, or a needle catheter, synthetic grafts, adventitial wraps, shunts and stents or other implantable devices, site specific carriers, direct injection, or direct application. See, e.g., WO 00/53211 and U.S. Pat. No. 5,981,568.

In another embodiment of the present disclosure, an article of manufacture is provided which contains any of the pharmaceutical compositions and formulations described herein (e.g., comprising an antibody or Binding Agent) and provides instructions for its use and/or reconstitution. The article of manufacture comprises a container. Suitable containers include, for example, bottles, vials (e.g. dual chamber vials), syringes (such as dual chamber syringes) and test tubes. The container may be formed from a variety of materials such as glass or plastic. The container holds the formulation and the label on, or associated with, the container may indicate directions for reconstitution and/or use. For example, the label may indicate that the formulation is reconstituted to particular protein concentrations. The container holding the formulation may be a multi-use vial, which allows for repeat administrations (e.g., from 2-6 administrations) of the reconstituted formulation. The article of manufacture may further comprise a second container comprising a suitable diluent (e.g. BWFI). Upon mixing of the diluent and the lyophilized formulation, the final protein concentration in the reconstituted formulation will generally be at least 50 mg/mL. The article of manufacture may further include other materials desirable from a commercial and user standpoint, including other buffers, diluents, filters, needles, syringes, and package inserts with instructions for use.

EXAMPLES

The following Examples are not limiting but only exemplary. Unless otherwise specified, all the secondary antibodies for detection were purchased from Jackson ImmunoResearch Laboratories (West Grove, Pa.).

To explore target-specific antibodies for the treatment of cancer, we used a live-cell immunization and live-cell high-throughput screening (HTS) technology to generate antibodies specifically targeting human tumor surface antigens, followed by identification of the targets using a combination of proteomic and molecular biological approaches.

Example 1

Generation of Monoclonal Antibodies by Live-Cell Immunization and Live-Cell High-Throughput Screening Monoclonal antibodies (mAbs) against the surface antigens of gastric cancer cells were generated using a live-cell immunization and live-cell high-throughput screening (HTS) technology as described by the inventors previously (see: WO2014146487A1, WO2017114204; Li et al., PLoS One. 2013, 8:e77398). Briefly, a mixture of four intact gastric cancer cell lines, MKN45, SGC7901, BGC823 and MKN28 (purchased from the Institute of Biochemistry and Cell Biology, Shanghai Institutes for Life Science, Chinese Academy of Science, Shanghai, China, and the Riken BioResource Center, Tsukuba, Japan), were used for a total of three immunization and one booster in A/J mice (The Jackson Laboratory, Bar Harbor, Me.). Mouse spleen cells were fused with mouse SP2/0 myeloma cells to generate hybridomas following the standard protocol (Kohler & Milstein, Nature 1975, 256:495-497; Winter & Milstein, Nature 1991, 349:293-299). The highly positive hybridoma colonies were selected for binding to the mixture of all four gastric cancer cell lines with low cross-reactivity to healthy human peripheral blood mononuclear cells (PBMC) using a BD FACSCalibur™ Flow Cytometer with High Throughput Sampler (FACS-HTS, Becton Dickinson, San Jose, Calif.) as described by Li et al. (PloS One 2013, 8:e77398). Hybridoma colonies that showed strong and specific binding activities to gastric cancer cells were selected for expansion, weaning from conditioned medium, and subcloning following standard protocols (Kohler & Milstein, Nature 1975, 256:495-497; Winter & Milstein, Nature 1991, 349:293-299).

Example 2

Identification of the Target Specifically Recognized by MAb1738 on the Gastric Cancer Cell Surface Sixteen highly positive hybridomas were isolated from a single batch of an antibody generation and screening experiment. One of the hybridomas, designated MA177-G1, was identified as an anti-PODXL-v2 antibody by a combinatory approach of immunoprecipitation (IP), sodium dodecyl sulfate polyacrylamide gel electrophoresis (SDS-PAGE), Western blot and matrix-assisted laser desorption ionization time-of-flight mass spectrometry (MALDI-TOF MS) analyses (See International Patent: WO2017114204). For an indirect IP procedure, 0.2 mL of Dynabeads™ Protein A for Immunoprecipitation (Thermo Fisher Scientific, Waltham, Mass.) was incubated with 50 μg of MAb1738 or an irrelevant antibody as an isotype antibody control in PBS at room temperature (RT) for 30 minutes. Two batches of the antibody-bound magnetic beads were then washed and incubated with the BGC823 or MKN45 gastric cancer cell lysate at RT for 30 minutes. The beads were sequentially washed with 0.5% TritonX-100/PBS and PBS buffers and the target proteins were then separated from the antibodies with 50 μL of Laemmli denaturing sample buffer in a boiling water bath for five minutes. The immunoprecipitated proteins were separated by SDS-PAGE and stained with Coomassie blue G250. An approximately 135-kDa band that corresponded to the size of the band detected by MA177-G1 in Western blot was excised from the gel and analyzed by MALDI-TOF. This procedure was repeated three times for reproducibility and consistency. The top four hits identified in all three experiments, including podocalyxin-like protein isoform 2 precursor (PODXL-v2), protein transport protein Sec16A, constitutive coactivator of peroxisome proliferator-activated receptor gamma (FAM120B), and SWI/SNF complex subunit SMARCC1, were selected and their gene-specific double-stranded small interfering RNA (siRNA) were synthesized (Thermo Fisher Scientific) and individually transfected into gastric cancer cells. The cell lysate samples were analyzed by Western blot using MAb1738 as the primary antibody and Horse Radish Peroxide (HRP)-conjugated Goat Anti-mouse IgG-Fc Polyclonal Antibody (pAb) (Jackson ImmunoResearch Laboratories) as the secondary antibody. β-actin was simultaneously detected with an anti-β-actin mAb (Jackson ImmunoResearch Laboratories) as a sample loading control.

Figure 1B:
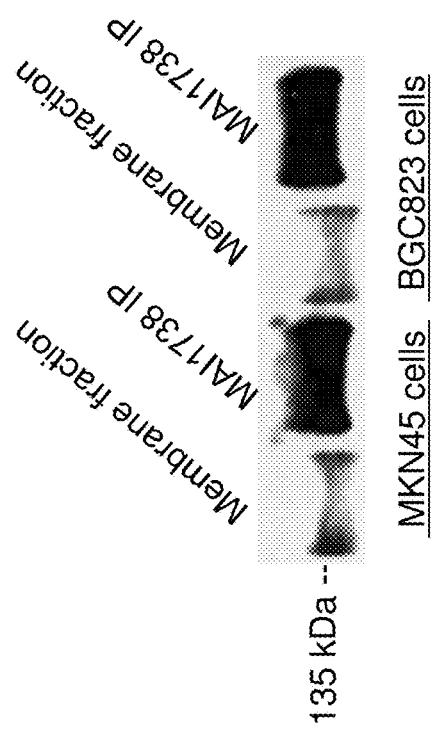
FIG. 1B is a Western blot showing that the 135-kDa bands precipitated by MAb1738 from both MKN45 and BGC823 cell membrane fractions could be detected by a commercially available Rabbit Anti-PODXL mAb, EPR9518 (Abcam, Cambridge, Mass.). IP: immunoprecipitation.

FIG. 1A shows that only the podxl-v2 siRNA could diminish the band detected by MAI1738 in the Western blot analysis, whereas the other three gene-specific siRNAs had no such effect. The RNAi result indicated that PODXL-v2 was the target for MAb1738. This result was further confirmed by Western blot using a commercially available anti-PODXL mAb, EPR9518 (Abcam, Cambridge, Mass.), which was able to detect the 135-kDa band in the IP samples precipitated by MAb1738 (FIG. 1B).

Example 3

Molecular Cloning of Light Chain and Heavy Chain Genes Encoding the Variable Regions of the MAb1738 mAb WO2017114204 revealed the cDNA and protein sequences of the variable regions of both the light and heavy chains of an MS17-38 subclone. Further cell staining analysis identified a second subclone, designated MAb1738, which had stronger binding affinity to the surface of gastric cancer cells than the previous subclone, renamed as MS17-38.1. The cDNA encoding the variable regions of both light and heavy chains of the MAb1738 subclone was also cloned and sequenced. See SEQ ID NO.:1 and SEQ ID NO.:3.

Total RNA was isolated from the MAb1738 hybridoma subclone using the PureLink® RNA Mini Kit (Thermo Fisher Scientific) and the first-strand cDNA library was reverse-transcribed using the High Capacity cDNA Reverse Transcription Kit (Thermo Fisher Scientific) following manufacturer's protocols. To amplify the cDNA fragments encoding the variable sequences of the light and heavy chains, a method described by O'Brien and Jones (O'Brien and Jones, 2001) was used. Briefly, the Mouse IgG Library Primer Set, which includes a set of 5' primers from the relatively conserved signal peptide regions and 3' primers from the constant regions of either the light chain or heavy chain, was purchased from Progen Biotechnik GmbH (Heidelberg, Germany). Each 5' primer was paired with the corresponding 3' primer in a single PCR reaction containing 2 μL of first-strand cDNA, 20 mM Tris-HCl (pH 8.4), 50 mM KCl, 1.5 mM $MgCl_2$, 0.2 mM of each dNTP, and thermostable Taq DNA Polymerase from the AccuPrime™ Taq DNA Polymerase System (Thermo Fisher Scientific). The PCR reactions were performed as follows: 1 cycle at 94° C. for 2 minutes, 25 cycles at 94° C. for 30 seconds, at 54° C. for 30 seconds, and at 72° C. for 30 seconds, followed by 1 cycle at 72° C. for 5 minutes. The PCR reaction mixtures were analyzed by electrophoresis in a 1% agarose gel and the amplified products were recovered with the GeneJET Gel Extraction Kit (Thermo Fisher Scientific). Amplified DNA fragments were cloned into the pMiniT2.0 vector (New England Biolabs, Ipswich, Mass.) following the manufacturer's protocol. Five colonies of each PCR-amplicon transformant were randomly selected for plasmid purification and DNA sequencing.

The sequencing results revealed that MAb1738 shared the same cDNA sequence encoding the heavy chain variable region with MS17-38.1 (SEQ ID NO.:3), but had a different cDNA sequence for the light chain variable region (SEQ ID NO.:1).

Example 4

Cloning and Sequencing of the PODXL-v2 cDNA in Gastric Cancer Cells

Total RNA was isolated from the BGC823 and MKN45 cells, respectively, using the PureLink® RNA Mini Kit and the reverse transcription reaction was carried out using the High Capacity cDNA Reverse Transcription Kit, as in Example 3. A pair of primers (SEQ ID NO: 5 and 6, below) complementary to the upstream and downstream of the podxl cDNA sequence (GeneBank Gene id: 5420) were used in a 50-μL PCR reaction mixture that contained 2 μL of the first-strand cDNA, 0.5 μM of each primer, 0.2 mM dNTP mix, and 1 U Q5 High-Fidelity DNA Polymerase with 1× reaction buffer. The PCR reaction was performed with an initial denaturation of 30 seconds at 98° C., 25 cycles of 98° C. for 10 seconds, 55° C. for 30 seconds and 72° C. for 60 seconds, followed by a final extension at 72° C. for 5 minutes. The PCR products were analyzed, gel-purified, and cloned into the pMiniT2.0 vector. Five colonies of each PCR-amplicon transformant were randomly selected for plasmid purification and DNA sequencing.

```
Forward Primer:
                                    (SEQ ID NO: 5)
5'-GACGACACGATGCGCTGCGC-3'

Reverse Primer:
                                    (SEQ ID NO: 6)
5'-GGCAGACCGGACTAGAGGTGTGTGT-3'
```

In addition to the podxl-v2 cDNA sequence that matched exactly with podxl-v2 published in GeneBank (ID: NM_005397.3), a mutant of podxl-v2 was also identified with two clones, one from each cell line. This mutant, designated as podxl-v2-del (SEQ ID NO: 7-8, below), contained three mutations in the N-terminal coding sequence including a C-to-T silent mutation for Leu$^{12}$ in the signal peptide sequence, a T-to-G mutation that changed Ser$^{23}$ to Ala$^{23}$ (S23A), and an in-frame deletion of six nucleotides encoding Ser$^{25}$ and Pro$^{26}$. The nucleotide sequences of podxl-v2, podxl-v2-del and podxl-v1 were compared using a pairwise algorism of the CLUSTAL 0 (1.2.4) program, see FIG. 2. The sequences shown in FIG. 2 are as follows: PODXL-v2-del (first row of each row in FIG. 2) SEQ ID NO: 10; PODXL-v2 (second row of each row in FIG. 2) SEQ ID NO: 11; PODXL-v1 (third row of each row in FIG. 2) SEQ ID NO: 12/It is worth mentioning that no podxl-v1 cDNA was amplified with either the primers flanking the entire podxl coding region, or with each of these primers paired with primers specific to the Exon 3 sequence that is only present in podxl-v1 but not in podxl-v2. This implied that the Exon 3 was likely removed during mRNA splicing and the PODXL-v1 protein was not expressed in these GC cell lines and therefore, the interaction between MAb1738 mAb and the gastric cancer cells was mediated by the extracellular domain of the PODXL-v2 or PODXL-v2-Del proteins. Similar 6-bp in-frame deletions in the podxl-v2 gene have been previously reported for their correlation with a poor prognosis for prostate cancer (Casey et al., 2006).

Example 5

Comparison of the Expression Levels of the Podxl-v2 Gene in Various Gastric Cancer (GC) Cell Lines Extraction of total RNA from PBMC and eight GC cell lines was performed using RNeasy mini kit (Qiagen). First-strand cDNA was synthesized using 2 µg/each total RNA as substrate in the presence of random hexamers using High-Capacity cDNA Reverse Transcription Kit (Applied Biosystems™, Thermo Fisher Biosciences). Real-time PCR was performed in the StepOnePlus™ Real-time PCR System (Applied Biosystems™) with TaqMan gene expression reagents containing probes and primers purchased from Applied Biosystems. IPO8 was used as a housekeeping gene and the data were normalized using the comparative Ct method.

Figure 3:
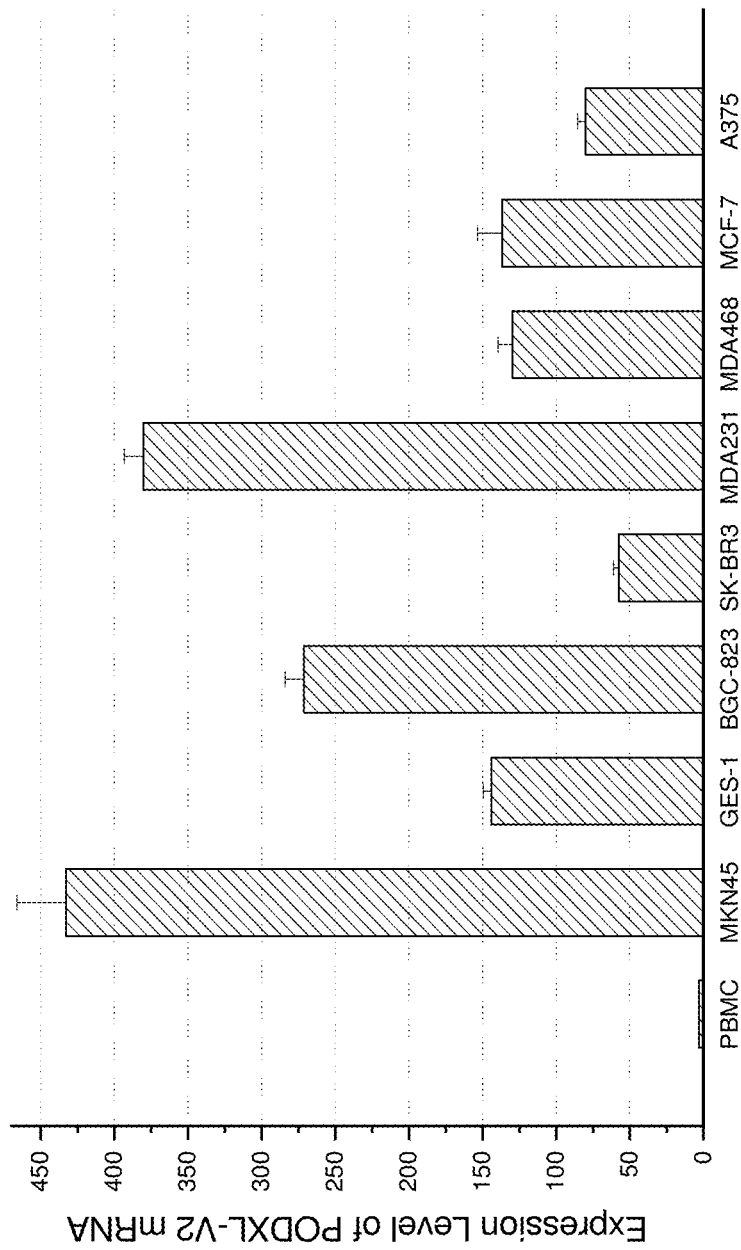
FIG. 3 illustrates that the expression levels of podxl-v2 mRNA in all eight GC cell lines were significantly elevated in comparison to PBMC expression levels. Gene expression was quantified by real-time RT-PCR using importin 8 (IPO8) as the reference gene. The data were normalized using the comparative Ct method. Each bar represents the average expression fold change±SD of triplicate samples.

As shown in FIG. 3, although varied greatly, the expression levels of podxl-v2 were significantly higher in all the eight GC cell lines than that in PBMC. MKN45, MDA231 and BGC823 showed the strongest expression of podxl-v2 and that was consistent with the cell staining results (data not shown).

Example 6

Immuocytochemistry (ICC) Analysis on Binding of MAb1738 with GC Cells

Fifty microliters of 1×10$^6$ GC cells was loaded into each cytospin chamber hole and were spun onto slides, followed by fixation with 4% paraformaldehyde/PBS solution, dehydration with 70% ethanol and then air drying. The slides were rehydrated in PBST in a flat position for 5 minutes and then incubated in 10% goat serum/PBS solution. The slides were incubated with MAb1738 or an irrelevant mAb (isotype control) for 1 hour at RT or overnight at 4° C., and then washed twice with PBST. The slides were then incubated with HRP-labeled goat anti-mouse IgG Fc-HRP (Jackson ImmunoResearch Laboratories) at 1:500 dilution for 30 minutes. Detection of mAb staining on cancer cells was performed with 0.125% aminoethylcarbazole chromogenic substrate for 5-10 minutes at RT, and the mAb stained cytospin slides were counterstained with Gill's hematoxylin (Dako, Carpinteria, Calif., USA).

Figure 4:
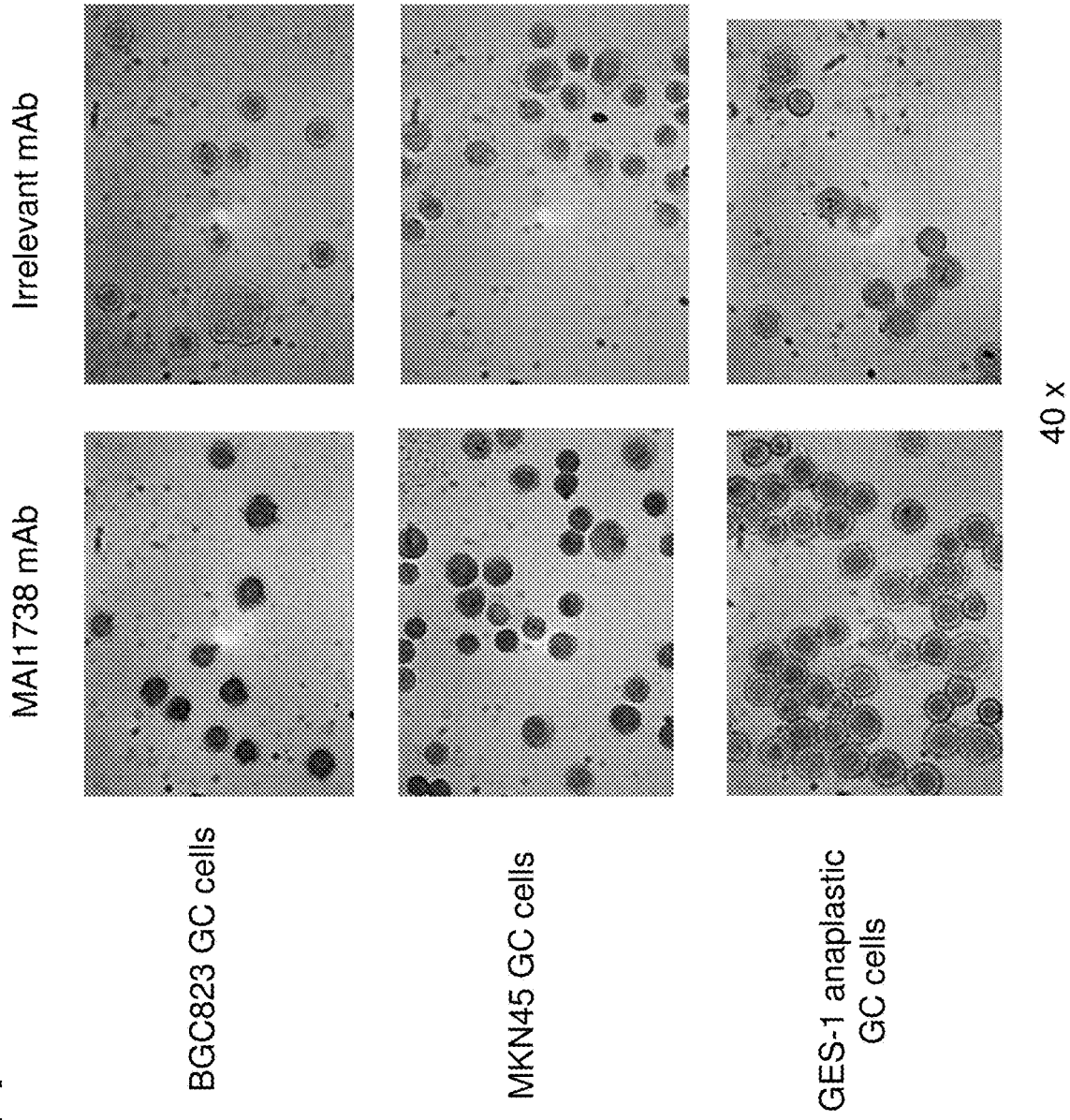
FIG. 4 shows representative images of immunocytochemistry (ICC) assay of BGC823, MKN45 and GES-1 GC cells on cytospin slides. MAb1738 bound specifically to the cell surfaces of all three types of GC cells. The isotype control (irrelevant mAb) did not bind to any of these cells. Images shown are at 40× magnification.

FIG. 4 shows that MAb1738 mAb could bind to all three GC cell lines tested, including BGC823, MKN45 and GES-1. The target was exclusively located on the surface of the cells. In contrast, the irrelevant mAb did not stain the cells. This makes MAb1738 a good candidate in targeting various GC cells with increased expression levels of PODXL-v2 and/or PODXL-v2-Del.

Example 7

Expression and Purification of the Extracellular Domains of PODXL-v2 and PODXL-v2-Del with Fc Fusion The DNA fragment encoding the extracellular domain of PODXL-v2 or PODXL-v2-Del was fused in-frame to the human IgG1-Fc DNA fragment in the pFUSE-hIgG1-Fc1 expression vector (InvivoGen, San Diego, Calif.) and transfected into CHO-K1 cells to select stable cell lines expressing the fusion protein. Stable cell lines were subcloned and cultured in home-made serum-free medium. The rPODXL-v2-Fc and rPODXL-v2-Del-Fc proteins were purified by Protein-A chromatography using MabSelect™ SuRe™ LX following the manufacturer's protocol (GE Healthcare Bio-Sciences AB, Uppsala Sweden). Both recombinant PODXL-Fc proteins were highly glycosylated with an apparent molecular weight of 150 kDa in reduced SDS-PAGE gel, and they could interact with MAb1738 mAb, but not any other irrelevant mAb (isotype controls), in a dose-dependent manner in both direct and indirect ELISA assays (data not shown).

Example 8

Binding to rPODXL-v2 and rPODXL-v2-Del by MAb1738 mAb

Figure 5:
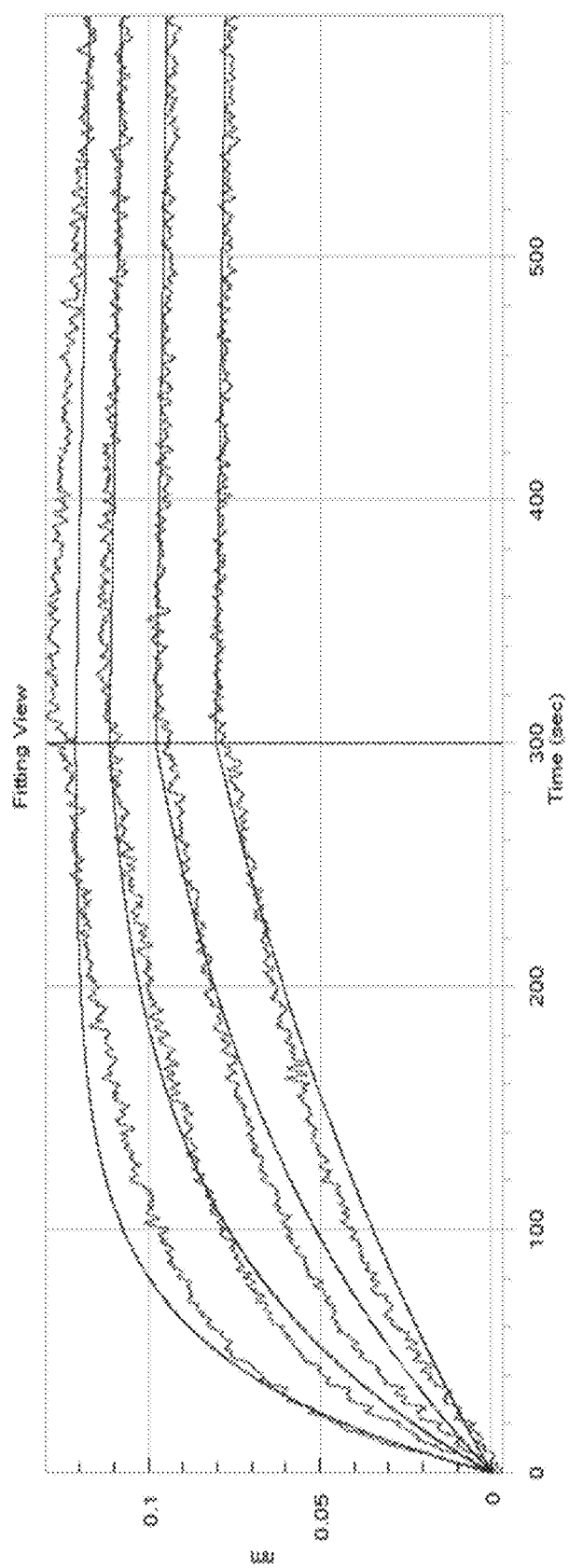
FIG. 5 shows the kinetic binding affinity of MAb1738 to the rPODXL-v2-Del-Fc fusion protein, which contained an in-frame fusion of the extracellular domain (ECD) of PODXL-v2-Del and the human IgG1 Fc region, was in nanomolar range, as measured by the Octet® QKe System (Molecular Devices, San Jose, Calif.).

The Octet® QKe System (Molecular Devices, San Jose, Calif.) was used to determine the binding affinities between MAb1738 mAb and the extracellular domains of PODXL-v2 and PODXL-v2-Del. The MAb1738 mAb was immobilized to the Anti-Mouse IgG Fc Capture (AMC) biosensors, followed by loading of the antigen, rPODXL-v2-Fc or rPODXL-v2-Del-Fc, at 1:2 serial dilutions for 5 minutes. The assay was repeated multiple times to determine the average range of the affinity between MAb1738 and rPODXL-v2-Fc or rPODXL-v2-Del-Fc. As shown in FIG. 5, the calculated $K_D$ for the MAb1738 and rPODXL-v2-Del-Fc interaction was $1.58 \times 10^{-9}$ M, similar to the MAI1738 and rPODXL-v2-Fc interaction (data not shown).

Example 9

Construction of the Expression Plasmids for MAb1738 Chimeric Antibody (chiAb) and Single Chain Variable Fragments (scFv)

The cDNA sequences encoding the variable regions of the light chain (VL) and heavy chain (VH) of MAb1738 were amplified with Q5® High-Fidelity DNA Polymerase (New England Biolabs, Ipswich, Mass.) and fused with the coding sequences of the constant regions of human kappa light chain (CL) and human IgG1 heavy chain (CH), respectively, by splicing by overlap extension polymerase chain reactions (SOE-PCR, Higuchi R et al., 1988). The full-length chimeric light chain or heavy chain PCR product was cloned into a pcDNA3.1 plasmid containing a signal peptide sequence. The plasmids were confirmed by restriction digestion and DNA sequencing. The light chain and heavy chain expression plasmids were co-transfected into HEK293 or CHO-K1 cells (ATCC, Manassas, Va.) at 2:1 ratio for transient expression for 4-5 days. The chimeric antibodies secreted to the culture medium were purified by affinity chromatography using MabSelect™ SuRe™ LX Protein A resin (GE Life Sciences, Pittsburgh, Pa.) and analyzed by SDS-PAGE.

MAb1738 chiAb showed similar binding affinity to both PODXL-v2-Fc and PODXL-v2-Del-Fc as did MAb1738 mAb; for both ELISA and cell staining assays measured with a FACSCalibur Flow Cytometer (Becton Dickinson, San Jose, Calif.) (data not shown).

The MAb1738 scFv constructs were cloned into the pcDNA3.1-derived expression vector by connection of the VL and VH cDNA sequences with a synthetic $(G4S)_3$ linker and addition of a C-terminal 6×His tag. The VL and VH genes were connected in either VL-VH or VH-VL order that were designated as MAb1738-LH-His or MAb1738-HL-His. The plasmids were transiently transfected into CHO-K1 cells and cultured for 5 days. Using HRP-conjugated Mouse Anti-6×His mAb (Proteintech Group, Rosemont, Ill.), the expression of both 6×His-tagged scFv proteins and their ability to in bind to PODXL-v2-Fc and PODXL-v2-Del-Fc were confirmed by Western blot and direct ELISA, respectively (data not shown).

Example 10

Inhibition of Proliferation of Gastric Cancer Cells by MAb1738 mAb

The effect of MAb1738 on the growth and proliferation of GC cells was evaluated with cell-based in vitro assays. The Cell Counting Kit-8 (CCK-8, Dojindo Molecular Technologies, Rockville, Md.) was used to determine cell viability following the manufacturer's protocol. Briefly, a total of $5 \times 10^3$ cells of each gastric cancer cell line were seeded in quadruplicate in seven 96-well plates and were incubated at 37° C. with 5% $CO_2$ for 24 hours. On Day 0 and Day 4, 50 μL of MAI1738 mAb or an irrelevant mAb (isotype control) at concentrations of 8 μg/mL, 30 μg/mL and 120 μg/mL, were added to the test plates and continued incubation. Cell viability was evaluated every 24 hours by incubation with 10 μL/well of CCK-8 solution for two hours and measurement of $OD_{450}$ with the VERSAmax Microplate Reader (Molecular Devices, San Jose, Calif.).

The CCK-8 assay results showed that MAI1738 could inhibit the proliferation of both MKN45 and BGC823 cell lines in a dose-dependent manner (FIG. 6), albeit the two cell lines showed different sensitivities to MAb1738; which was likely due to different expression levels of PODXL-v2 on these two cell lines.

Example 11

Inhibition of Cell Migration and Invasion of Gastric Cancer Cells by MAb1738 mAb or PODXL-Specific siRNA Although the function of PODXL-v2 is still unclear, it has been proposed to be related to poor prognosis of cancer (Casey et al., 2006). Since PODXL-v1 is known to be involved in cell movement (Lee et al., 2009), we presumed that the expression of PODXL-v2 or PODXL-v2-Del on tumor cells might also play a role in tumor migration, and thus the metastasis of tumors. A migration assay was therefore conducted to determine whether MAb1738 could interfere with the migration of GC cells through a Transwell membrane. The migration of cancer cells in vitro was assessed using the 8 μm QCM™ 24-Well Colorimetric Cell Migration Assay Kit (EMD Millipore, Burlington, Mass.). Three hundred microliters of $3 \times 10^4$ cells in serum-free medium was mixed with 100 μg/mL MAb1738 or the irrelevant mAb and seeded to each insert, followed by addition of 500 μL/well of serum-free medium containing 5% FBS to the lower chamber. The plates were incubated at 37° C. with 5% $CO_2$ for 24 hours. Non-migrating cells were gently and completely removed from the interior of the inserts using cotton-tipped swabs. The migrated cells on the lower side of the inserts were stained by dipping the inserts into wells containing 400 μL/well of Cell Stain at room temperature for 20 minutes. The inserts of the washed and stained cells were photographed, and the stained cells extracted using Extraction Buffer and then quantified with the VERSAmax Microplate Reader. The invasion of GC cells was evaluated with a similar protocol using the QCM ECMatrix cell Invasion Assay Kit (EMD Millipore, Burlington, Mass.). The ECM layer occludes the membrane pores, blocking non-invasive cells from migrating. Invasive cells, on the other hand, migrate through the ECM layer and cling to the bottom of the membrane.

Figure 7A:
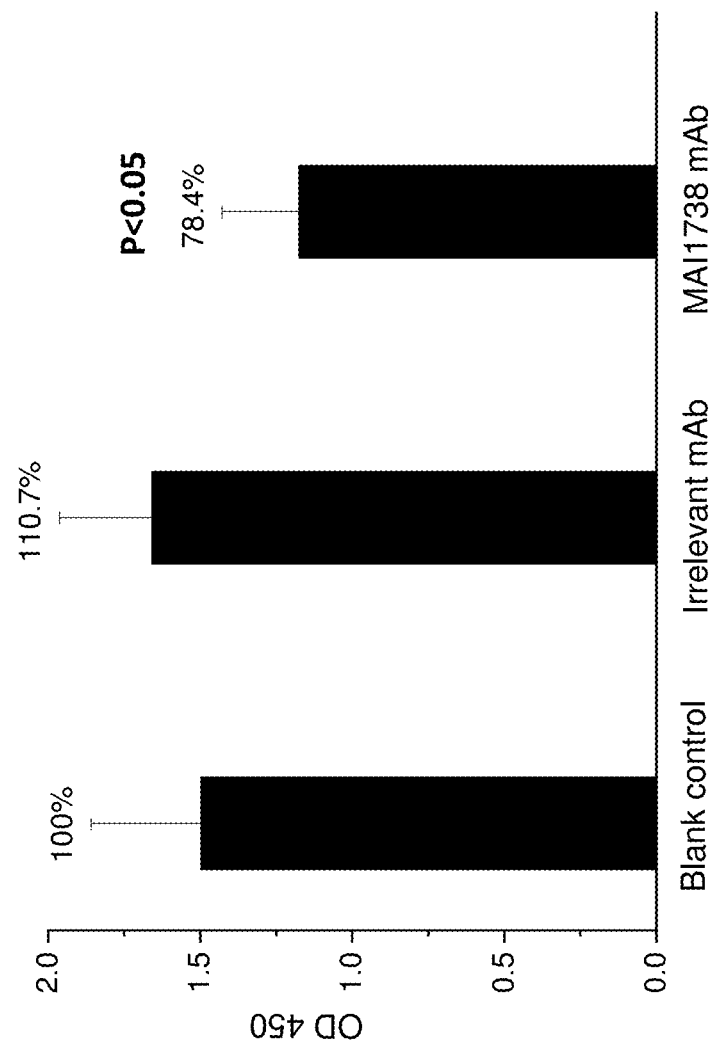
Figure 8B:
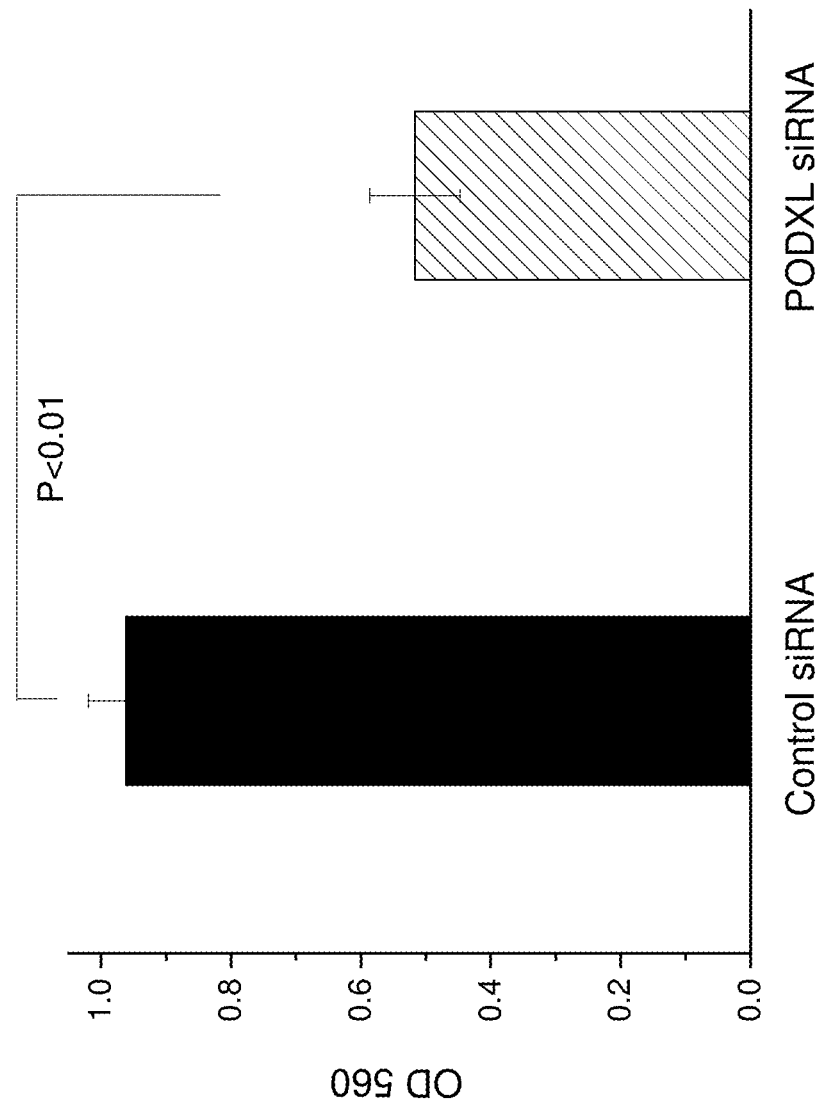

Compared with culture medium and the irrelevant mAb controls, 150 μg/mL of MAb1738 were effective in inhibiting the migration of the BGC823 cells (P<0.05, FIG. 7A). An invasion assay, which employed the CytoSelect™ Cell Invasion Assay System, demonstrated that, by comparison with an irrelevant mAb, MAb1738 effectively blocked the invasion of the MKN45 cells into the basement membrane-coated inserts (FIG. 7C). Furthermore, both proliferation and migration of the MKN-45 cells could be inhibited by transfection of PODXL-v2 siRNA (FIGS. 8A to 8C), which abolished the expression of the PODXL-v2/PODXL-v2-Del proteins. Taken together, these results suggested that both the MAb1738 mAb and PODXL-v2 siRNA could specifically prevent cell growth and block the migration of the MKN45 cells.

Example 12

Inhibition of Gastric Cancer Tumor Growth by MAb1738 in Xenograft nu/nu Mouse Models In vitro studies showed that MAb1738 inhibited the growth and proliferation of GC cells (FIG. 7). Subsequently, an MKN45 xenograft model was employed using nu/nu mice to evaluate the effect of MAb1738 on GC tumors. Each nu/nu mouse was subcutaneously (s.c.) injected with 2×10⁶ GC cells into the flank for the tumor growth model as previously described (Li et al., 2013). Approximately five days after injection, when small tumor nodules were detectable at the sites of injection, the mice were randomly divided into two or three groups followed by intraperitoneal (i.p.) injection with MAb1738 (the treatment group), the irrelevant mAb (the isotype control group), or PBS (the blank control group) every three or five days for a total of seven or eight doses. The diameters of the subcutaneous nodules along with the vital signs and weights of the mice were measured before and during each treatment. The three dimensions and weights of the subcutaneous nodules were measured after the mice were sacrificed.

Figure 9A:
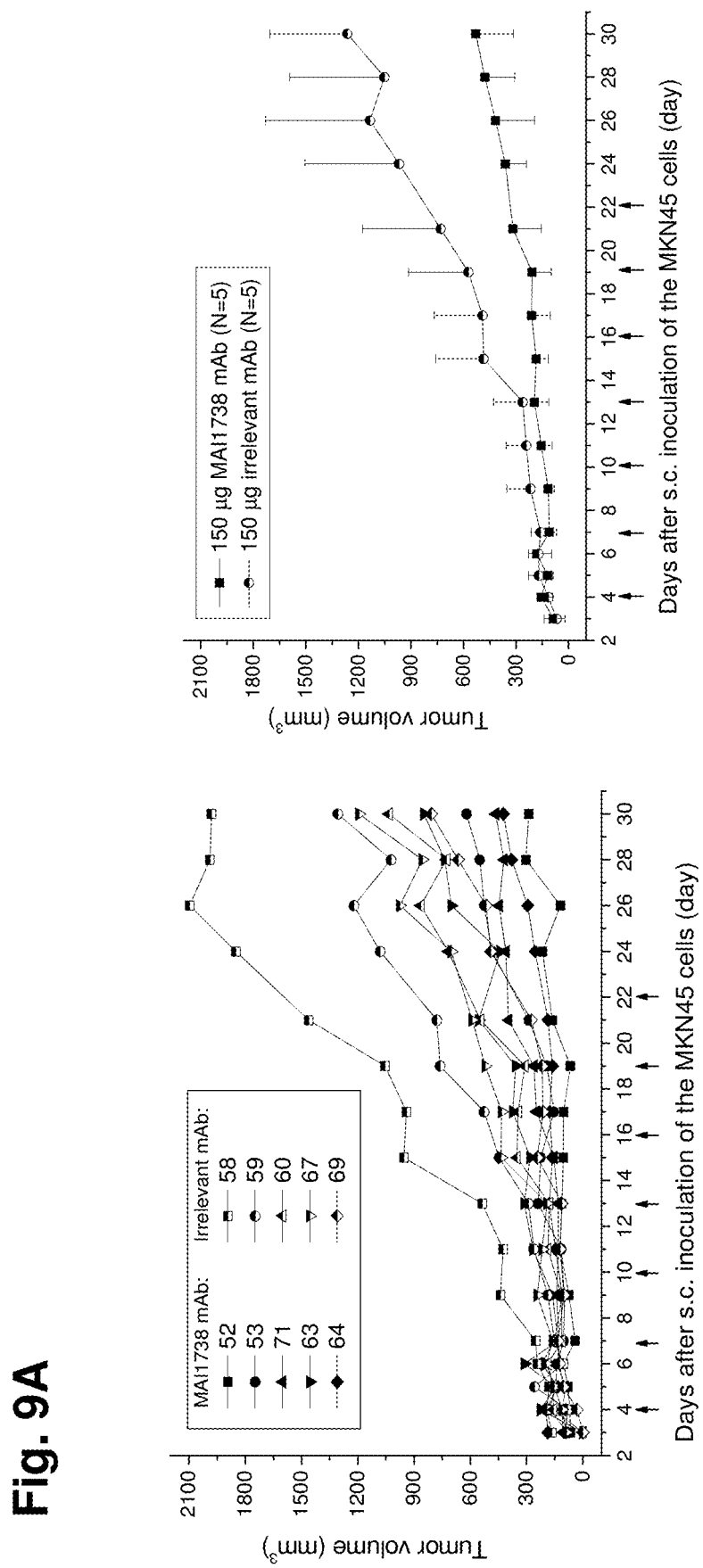
Figure 9C:
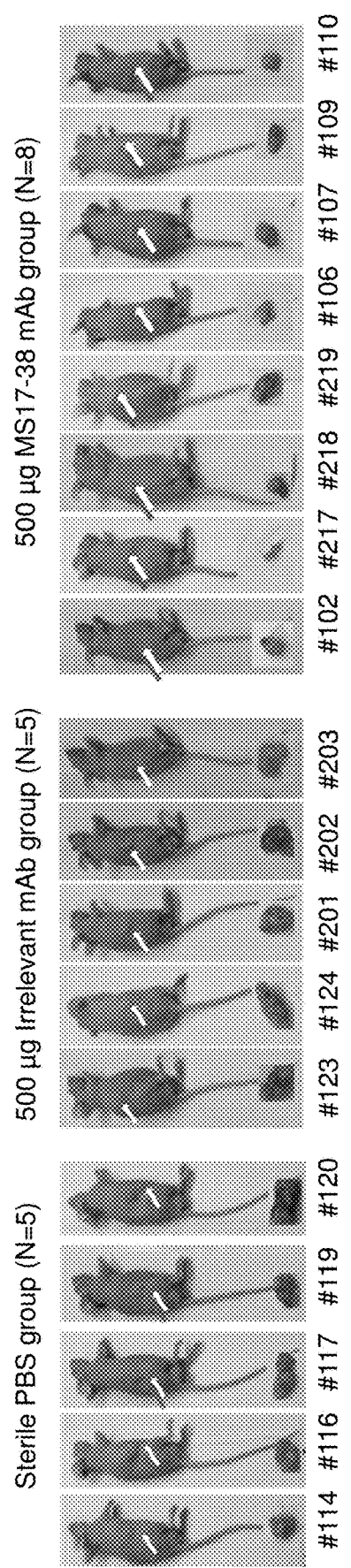

In a pilot in vivo study, the MKN-45 cells were injected subcutaneously (s.c.) into the flank of nu/nu mice. After the tumors were established, the animals were randomized and 150 μg of MAb1738 (the treatment group) or an irrelevant mAb (the isotype control group) was administered to each mouse via intraperitoneal (i.p.) injection at three-day intervals for eight doses in total. The diameters of the tumors were measured and the vital signs and weights of the mice were observed daily. Differences in tumor volumes between these two groups could be observed after the fourth dose and became more evident over time (P<0.05, FIG. 9A).

A second in vivo study was carried out with a different treatment regimen by i.p. injection with 300 μg of MAb1738 to each of the eight mice in the treatment group, or 300 μg of the irrelevant mAb to each of the five mice in the isotype control group, at five-day intervals for a total of ten doses. In addition, another five mice were injected with the same volumes of PBS as blank controls. FIG. 9B illustrates that tumors in both control groups continued to grow, but in contrast, the tumors in the MAb1738 treatment group showed much slower growth rate with statistical significance (P<0.01); and the sizes of the tumors were much smaller in the treatment group than those of the two control groups, supporting the hypothesis that MAb1738 inhibited GC tumor growth in vivo.

Example 13

Inhibition of Gastric Cancer Metastasis by MAb1738 in Xenograft nu/nu Mouse Models For the cancer metastasis model, the nu/nu mice were randomized into three groups for pre-treated with 300 μg/mouse of MAb1738, the irrelevant mAb and an equal volume of PBS, respectively. Each mouse was injected with 1×10⁶ of the MKN-45 cells into the tail vein (i.v.) 24 hours later and continued to receive treatment with the corresponding agent for 10 weeks at four-days intervals. The weights of the mice were monitored before and during each treatment. The mice were sacrificed at Day 65 and the lungs were sliced and stained with hematoxylin and eosin (HE) to count the metastatic tumor colonies.

All the mice in the blank control group and seven out of eight mice in the isotype control group were found to bear metastatic nodules in the lungs, whereas, strikingly, only one out of ten mice in the MAb1738_-treatment group had tumor nodules in the lung (FIG. 10). The difference between the treatment group and the two control groups was statistically different (P<0.01), suggesting that MAb1738 could prevent/inhibit the metastasis of GC cells and could be used for the development of therapeutic antibodies for gastric cancer and other cancer types that overexpress PODXL.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "including", containing", etc. are to be read expansively and without limitation. The methods and processes illustratively described herein suitably may be practiced in differing orders of steps, and that they are not necessarily restricted to the orders of steps indicated herein or in the claims. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The invention has been described broadly and generically herein. Each of the narrower species and subgeneric groupings falling within the generic disclosure also form part of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Full sequences of PODXL-v1; PODXL-v2; PODXL-v2-Del
>PODXL-v1
(SEQ ID NO.: 13)
GACGACACGATGCGCTGCGCGCTGGCGCTCTCGGCGCTGCTGCTACTGTT

GTCAACGCCGCCGCTGCTGCCGTCGTCGCCGTCGCCGTCGCCGTCGCCCT

CCCAGAATGCAACCCAGACTACTACGGACTCATCTAACAAAACAGCACCG

ACTCCAGCATCCAGTGTCACCATCATGGCTACAGATACAGCCCAGCAGAG

CACAGTCCCCACTTCCAAGGCCAACGAAATCTTGGCCTCGGTCAAGGCGA

CCACCCTTGGTGTATCCAGTGACTCACCGGGGACTACAACCCTGGCTCAG

CAAGTCTCAGGCCCAGTCAACACTACCGTGGCTAGAGGAGGCGGCTCAGG

CAACCCTACTACCACCATCGAGAGCCCCAAGAGCACAAAAAGTGCAGACA

CCACTACAGTTGCAACCTCCACAGCCACAGCTAAACCTAACACCACAAGC

AGCCAGAATGGAGCAGAAGATACAACAAACTCTGGGGGGAAAAGCAGCCA

CAGTGTGACCACAGACCTCACATCCACTAAGGCAGAACATCTGACGACCC

-continued

```
CTCACCCTACAAGTCCACTTAGCCCCCGACAACCCACTTCGACGCATCCT
GTGGCCACCCCAACAAGCTCGGGACATGACCATCTTATGAAAATTTCAAG
CAGTTCAAGCACTGTGGCTATCCCTGGCTACACCTTCACAAGCCCGGGGA
TGACCACCACCCTACTAGAGACAGTGTTTCACCATGTCAGCCAGGCTGGT
CTTGAACTCCTGACCTCGGGTGATCTGCCCACCTTGGCCTCCCAAAGTGC
TGGGATTACAGCGTCATCGGTTATCTCGCAAAGAACTCAACAGACCTCCA
GTCAGATGCCAGCCAGCTCTACGGCCCCTTCCTCCCAGGAGACAGTGCAG
CCCACGAGCCCGGCAACGGCATTGAGAACACCTACCCTGCCAGAGACCAT
GAGCTCCAGCCCCACAGCAGCATCAACTACCCACCGATACCCCAAAACAC
CTTCTCCCACTGTGGCTCATGAGAGTAACTGGGCAAAGTGTGAGGATCTT
GAGACACAGACACAGAGTGAGAAGCAGCTCGTCCTGAACCTCACAGGAAA
CACCCTCTGTGCAGGGGGCGCTTCGGATGAGAAATTGATCTCACTGATAT
GCCGAGCAGTCAAAGCCACCTTCAACCCGGCCCAAGATAAGTGCGGCATA
CGGCTGGCATCTGTTCCAGGAAGTCAGACCGTGGTCGTCAAAGAAATCAC
TATTCACACTAAGCTCCCTGCCAAGGATGTGTACGAGCGGCTGAAGGACA
AATGGGATGAACTAAAGGAGGCAGGGGTCAGTGACATGAAGCTAGGGGAC
CAGGGGCCACCGGAGGAGGCCGAGGACCGCTTCAGCATGCCCCTCATCAT
CACCATCGTCTGCATGGCATCATTCCTGCTCCTCGTGGCGGCCCTCTATG
GCTGCTGCCACCAGCGCCTCTCCCAGAGGAAGGACCAGCAGCGGCTAACA
GAGGAGCTGCAGACAGTGGAGAATGGTTACCATGACAACCCAACACTGGA
AGTGATGGAGACCTCTTCTGAGATGCAGGAGAAGAAGGTGGTCAGCCTCA
ACGGGGAGCTGGGGACAGCTGGATCGTCCCTCTGGACAACCTGACCAAG
GACGACCTGGATGAGGAGGAAGACACACACCTCTAG
```

>PODXL-v2

(SEQ ID NO.: 14)
```
GACGACACGATGCGCTGCGCGCTGGCGCTCTCGGCGCTGCTGCTACTGTT
GTCAACGCCGCCGCTGCTGCCGTCGTCGCCGTCGCCGTCGCCGTCGCCCT
CCCAGAATGCAACCCAGACTACTACGGACTCATCTAACAAAACAGCACCG
ACTCCAGCATCCAGTGTCACCATCATGGCTACAGATACAGCCCAGCAGAG
CACAGTCCCCACTTCCAAGGCAACGAAATCTTGGCCTCGGTCAAGGCGA
CCACCCTTGGTGTATCCAGTGACTCACCGGGGACTACAACCCTGGCTCAG
CAAGTCTCAGGCCCAGTCAACACTACCGTGGCTAGAGGAGGCGGCTCAGG
CAACCCTACTACCACCATCGAGAGCCCAAGAGCACAAAAAGTGCAGACA
CCACTACAGTTGCAACCTCCACAGCCACAGCTAAACCTAACACCACAAGC
AGCCAGAATGGAGCAGAAGATACAACAAACTCTGGGGGGAAAAGCAGCCA
CAGTGTGACCACAGACCTCACATCCACTAAGGCAGAACATCTGACGACCC
CTCACCCTACAAGTCCACTTAGCCCCCGACAACCCACTTCGACGCATCCT
GTGGCCACCCCAACAAGCTCGGGACATGACCATCTTATGAAAATTTCAAG
CAGTTCAAGCACTGTGGCTATCCCTGGCTACACCTTCACAAGCCCGGGGA
TGACCACCACCCTACCGTCATCGGTTATCTCGCAAAGAACTCAACAGACC
TCCAGTCAGATGCCAGCCAGCTCTACGGCCCCTTCCTCCCAGGAGACAGT
GCAGCCCACGAGCCCGGCAACGGCATTGAGAACACCTACCCTGCCAGAGA
```

```
CCATGAGCTCCAGCCCCACAGCAGCATCAACTACCCACCGATACCCCAAA
ACACCTTCTCCCACTGTGGCTCATGAGAGTAACTGGGCAAAGTGTGAGGA
TCTTGAGACACAGACACAGAGTGAGAAGCAGCTCGTCCTGAACCTCACAG
GAAACACCCTCTGTGCAGGGGGCGCTTCGGATGAGAAATTGATCTCACTG
ATATGCCGAGCAGTCAAAGCCACCTTCAACCCGGCCCAAGATAAGTGCGG
CATACGGCTGGCATCTGTTCCAGGAAGTCAGACCGTGGTCGTCAAAGAAA
TCACTATTCACACTAAGCTCCCTGCCAAGGATGTGTACGAGCGGCTGAAG
GACAAATGGGATGAACTAAAGGAGGCAGGGGTCAGTGACATGAAGCTAGG
GGACCAGGGGCCACCGGAGGAGGCCGAGGACCGCTTCAGCATGCCCCTCA
TCATCACCATCGTCTGCATGGCATCATTCCTGCTCCTCGTGGCGGCCCTC
TATGGCTGCTGCCACCAGCGCCTCTCCCAGAGGAAGGACCAGCAGCGGCT
AACAGAGGAGCTGCAGACAGTGGAGAATGGTTACCATGACAACCCAACAC
TGGAAGTGATGGAGACCTCTTCTGAGATGCAGGAGAAGAAGGTGGTCAGC
CTCAACGGGGAGCTGGGGACAGCTGGATCGTCCCTCTGGACAACCTGAC
CAAGGACGACCTGGATGAGGAGGAAGACACACACCTCTAG
```

>PODXL-v2-Del (SEQ ID NO.: 15)
```
GACGACACGATGCGCTGCGCGCTGGCGCTCTCGGCGCTGCTGtTACTGTT
GTCAACGCCGCCGCTGCTGCCGTCGgCGCCGTCGCCGTCGCCCTCCCAGA
ATGCAACCCAGACTACTACGGACTCATCTAACAAAACAGCACCGACTCCA
GCATCCAGTGTCACCATCATGGCTACAGATACAGCCCAGCAGAGCACAGT
CCCCACTTCCAAGGCCAACGAAATCTTGGCCTCGGTCAAGGCGACCACCC
TTGGTGTATCCAGTGACTCACCGGGGACTACAACCCTGGCTCAGCAAGTC
TCAGGCCCAGTCAACACTACCGTGGCTAGAGGAGGCGGCTCAGGCAACCC
TACTACCACCATCGAGAGCCCAAGAGCACAAAAAGTGCAGACACCACTA
CAGTTGCAACCTCCACAGCCACAGCTAAACCTAACACCACAAGCAGCCAG
AATGGAGCAGAAGATACAACAAACTCTGGGGGGAAAAGCAGCCACAGTGT
GACCACAGACCTCACATCCACTAAGGCAGAACATCTGACGACCCCTCACC
CTACAAGTCCACTTAGCCCCCGACAACCCACTTCGACGCATCCTGTGGCC
ACCCCAACAAGCTCGGGACATGACCATCTTATGAAAATTTCAAGCAGTTC
AAGCACTGTGGCTATCCCTGGCTACACCTTCACAAGCCCGGGGATGACCA
CCACCCTACCGTCATCGGTTATCTCGCAAAGAACTCAACAGACCTCCAGT
CAGATGCCAGCCAGCTCTACGGCCCCTTCCTCCCAGGAGACAGTGCAGCC
CACGAGCCCGGCAACGGCATTGAGAACACCTACCCTGCCAGAGACCATGA
GCTCCAGCCCCACAGCAGCATCAACTACCCACCGATACCCCAAAACACCT
TCTCCCACTGTGGCTCATGAGAGTAACTGGGCAAAGTGTGAGGATCTTGA
GACACAGACACAGAGTGAGAAGCAGCTCGTCCTGAACCTCACAGGAAACA
CCCTCTGTGCAGGGGGCGCTTCGGATGAGAAATTGATCTCACTGATATGC
CGAGCAGTCAAAGCCACCTTCAACCCGGCCCAAGATAAGTGCGGCATACG
GCTGGCATCTGTTCCAGGAAGTCAGACCGTGGTCGTCAAAGAAATCACTA
TTCACACTAAGCTCCCTGCCAAGGATGTGTACGAGCGGCTGAAGGACAAA
```

-continued

```
TGGGATGAACTAAAGGAGGCAGGGGTCAGTGACATGAAGCTAGGGGACCA

GGGGCCACCGGAGGAGGCCGAGGACCGCTTCAGCATGCCCCTCATCATCA

CCATCGTCTGCATGGCATCATTCCTGCTCCTCGTGGCGGCCCTCTATGGC

TGCTGCCACCAGCGCCTCTCCCAGAGGAAGGACCAGCAGCGGCTAACAGA

GGAGCTGCAGACAGTGGAGAATGGTTACCATGACAACCCAACACTGGAAG

TGATGGAGACCTCTTCTGAGATGCAGGAGAAGAAGGTGGTCAGCCTCAAC

GGGGAGCTGGGGGACAGCTGGATCGTCCCTCTGGACAACCTGACCAAGGA

CGACCTGGATGAGGAGGAAGACACACACCTCTAG
```

INCORPORATION BY REFERENCE

All patents and patent applications cited herein are hereby incorporated by reference, as are all other references cited.

CITATIONS TO NON-PATENT LITERATURE CITED IN THE DESCRIPTION BY NAME OF AUTHOR(S) ONLY

Boman K, Andersson G, Wennersten C, Nodin B, Ahlgren G, Jirström K. Biomark Res. 2017; 5:10

Bray F, Ferlay J, Soerjomataram I, Siegel R L, Torre L A, Jemal A. C A Cancer J Clin. 2018; 68:394-424

Casey G, Neville P J, Liu X, Plummer S J, Cicek M S, Krumroy L M, Curran A P, McGreevy M R, Catalona W J, Klein E A, Witte J S. Hum Mol Genet 2006, 15:735-741.

Forse C L, Yilmaz Y E, Pinnaduwage D, O'Malley F P, Mulligan A M, Bull S B, Andrulis I L. Breast Cancer Res Treat. 2013; 137:709-719

Fuchs C S, Tomasek J, Yong C J, Dumitru F, Passalacqua R, Goswami C, Safran H, Dos Santos L V, Aprile G, Ferry D R, Melichar B, Tehfe M1, Topuzov E, Zalcberg J R, Chau I, Campbell W, Sivanandan C, Pikiel J, Koshiji M, Hsu Y, Liepa A M, Gao L, Schwartz J D, Tabernero J; REGARD Trial Investigators. Lancet. 2014; 383:31-39

Higuchi R, Krummel B, and Saiki R. Nucleic Acids Res 1988; 16:7351-7367

Kohler & Milstein. Nature 1975; 256:495-497

Larsson A, Fridberg M, Gaber A, Nodin B, Levéen P, Jönsson G, Uhlén M, Birgisson H, Jirström K. BMC Cancer. 2012; 12:282

Lee R H, Seo M J, Pulin A A, Gregory C A, Ylostalo J, Prockop D J. Blood. 2009; 113:816-826.

Li M, Gao J, Feng R, Wang Y, Chen X, Sun J, Zhang D, Zhu Z, Ellis L M, Lu M, Lee J E, Feng Z, Liu B. PLoS One. 2013; 8:e77398

Nielsen and McNagny, J Am Soc Nephrol. 2009; 20:1669-1676

O'Brien and Jones, Humanizing antibodies by CDR grafting, Antibody Engineering, Springer Lab manual, Eds. Kontermann and Double, 2001

Sahin U, Schuler M, Richly H, Bauer S, Krilova A, Dechow T, Jerling M, Utsch M, Rohde C, Dhaene K, Huber C, Türeci Ö. Eur J Cancer. 2018; 100:17-26

Snyder K A, Hughes M R, Hedberg B, Brandon J, Hernaez D C, Bergqvist P, Cruz F, Po K, Graves M L, Turvey M E, Nielsen J S, Wilkins J A, McColl S R, Babcook J S, Roskelley C D, McNagny K M. Breast Cancer Res. 2015; 17:46

Taniuchi K, Furihata M, Naganuma S, Dabanaka K, Hanazaki K, Saibara T. Cancer Sci. 2016; 107:1430-1442

Wilke H, Muro K, Van Cutsem E, Oh S C, Bodoky G, Shimada Y, Hironaka S, Sugimoto N, Lipatov O, Kim T Y, Cunningham D, Rougier P, Komatsu Y, Ajani J, Emig M, Carlesi R, Ferry D, Chandrawansa K, Schwartz J D, Ohtsu A; RAINBOW Study Group. Lancet Oncol. 2014; 15:1224-1235

Winter & Milstein. Nature 1991; 349:293-299

What is claimed is:

1. An antibody that specifically binds to podocalyxin-like protein precursor isoform 2 (PODXL-v2), comprising wherein CDR1 to CDR3 of the light chain variable region respectively having sequences identical to SEQ ID NO:7, SEQ ID NO:8 and SEQ ID NO:9, and CDR1 to CDR3 of the heavy chain variable region respectively having sequences identical to SEQ ID NO:19, SEQ ID NO:20 and SEQ ID NO:21.

2. The antibody of claim 1 having a light chain variable region which is SEQ ID NO.: 2.

3. The antibody of claim 1 having a heavy chain variable region which is to SEQ ID NO.:4.

4. An isolated DNA or RNA molecule encoding the light chain variable region of the antibody of claim 1.

5. An isolated DNA molecule of claim 4 having the nucleotide sequence of SEQ ID NO: 1.

6. An isolated DNA molecule of claim 4 having the nucleotide sequence of SEQ ID NO:3.

7. The the antibody of claim 1 which is a monoclonal antibody.

8. The monoclonal antibody of claim 7 which is a murine, humanized, chimeric, bispecific, or multispecific or linear antibody.

9. The antibody of claim 1 which is a diabody, or a single domain antigen binding (SDAB) molecule.

10. The monoclonal antibody of claim 8 which has an IgG1 heavy chain and κ light chain.

11. The antibody of claim 1 which is a Fab, Fab', F(ab')2, Facb, Fv, or Fd fragment.

12. The antibody of claim 1 which is a scFv or a sc(Fv)2.

13. The monoclonal antibody of claim 8 which is class: IgD, IgE, IgG, IgA, or IgM, or a sub-class of one of said classes.

14. The monoclonal antibody of claim 13 wherein the sub-class is IgG1, IgG2, IgG3, IgG4, IgA1 or IgA2.

15. The monoclonal antibody of claim 13 having a κ light chain.

16. A vector comprising an isolated DNA molecule of claim 4.

17. The vector of claim 16 transfected into a host cell.

18. The vector of claim 17 wherein the host cell is murine.

19. An isolated DNA or RNA molecule encoding the heavy chain variable region of a binding agent of claim 1.

20. A vector comprising an isolated DNA molecule of claim 19.

* * * * *

SEQUENCE LISTING

```
<160> NUMBER OF SEQ ID NOS: 21

<210> SEQ ID NO 1
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
gatattgtgc taactcagtc tccagtcacc ctgtctgtga ctccaggaga tagcgtcagt      60
ctttcctgca gggccagcca aagtattaac aacaacctac actggtatca acaaaaatca    120
catgagtctc caaggcttct catcaagtat gcttcccagt ccatctctgg gatcccccc     180 aggttcagtg gcagtcgatc agggacagat ttcactctca gtatcaacac tgtggagact    240
gaagattttg gagtttattt ctgtcaacag agtaacagtt ggccgctcac gttcggtgct    300
gggaccaagc tggagctgaa acgggctgat gctgcaccaa ctgtatcc                 348

<210> SEQ ID NO 2
<211> LENGTH: 116
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 2

Asp Ile Val Leu Thr Gln Ser Pro Val Thr Leu Ser Val Thr Pro Gly
1               5                   10                  15

Asp Ser Val Ser Leu Ser Cys Arg Ala Ser Gln Ser Ile Asn Asn Asn
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Pro Arg Phe Ser Gly
    50                  55                  60

Ser Arg Ser Gly Thr Asp Phe Thr Leu Ser Ile Asn Thr Val Glu Thr
65                  70                  75                  80

Glu Asp Phe Gly Val Tyr Phe Cys Gln Gln Ser Asn Ser Trp Pro Leu
                85                  90                  95

Thr Phe Gly Ala Gly Thr Lys Leu Glu Leu Lys Arg Ala Asp Ala Ala
            100                 105                 110

Pro Thr Val Ser
        115

<210> SEQ ID NO 3
<211> LENGTH: 388
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
gaggtgaagc tggtggagtc tgggggaggc ttagtgaagc ctggagggtc cctgaaagtc      60
tcctgtgcag cctctggatt cactttcagt acctatacca tgtcttgggt tcgccagact     120
ccggagaaga ggctggagtg ggtcgcaacc attagtggtg gtgttattta cacctactat     180
ccagacagtg tgaagggccg attcaccatc tccagagacg atgccaagaa cactctgtat     240
ctgcaaatga gcagtctgag gtctgaggac acggccttgt attactgtgc aagacactat     300
agtaactacg agggccaagg tatggactcc tggggtcaag aacctcagt caccgtctcc     360 tcagccaaaa cgacaccccc atctgaca                                        388

<210> SEQ ID NO 4
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Glu Val Lys Leu Val Glu Ser Gly Gly Gly Leu Val Lys Pro Gly Gly
1               5                   10                  15

Ser Leu Lys Val Ser Cys Ala Ala Ser Gly Phe Thr Phe Ser Thr Tyr
            20                  25                  30

Thr Met Ser Trp Val Arg Gln Thr Pro Glu Lys Arg Leu Glu Trp Val
        35                  40                  45

Ala Thr Ile Ser Gly Gly Val Ile Tyr Thr Tyr Tyr Pro Asp Ser Val
    50                  55                  60

Lys Gly Arg Phe Thr Ile Ser Arg Asp Asp Ala Lys Asn Thr Leu Tyr
65                  70                  75                  80

```
Leu Gln Met Ser Ser Leu Arg Ser Glu Asp Thr Ala Leu Tyr Tyr Cys
                85                  90                  95

Ala Arg His Tyr Ser Asn Tyr Glu Gly Gln Gly Met Asp Ser Trp Gly
            100                 105                 110

Gln Gly Thr Ser Val Thr Val Ser Ser Ala Lys Thr Thr Pro Pro Ser
        115                 120                 125

Asp

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gacgacacga tgcgctgcgc                                              20

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggcagaccgg actagaggtg tgtgt                                        25

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Ala Ser Gln Ser Ile Asn Asn Asn Leu His
1               5                   10

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Tyr Ala Ser Gln Ser Ile Ser
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Gln Ser Asn Ser Trp Pro Leu Thr
1               5
```

<210> SEQ ID NO 10
<211> LENGTH: 1686
<212> TYPE: DNA
<213> ORGANISM: Homo sapiens

<400> SEQUENCE: 10

| | | | | | |
|---|---|---|---|---|---|
| gacgacacga | tgcgctgcgc | gctggcgctc | tcggcgctgc | tgctactgtt | gtcaacgccg | 60 |
| ccgctgctgc | cgtcgtcgcc | gtcgccgtcg | ccgtcgccct | cccagaatgc | aacccagact | 120 |
| actacggact | catctaacaa | aacagcaccg | actccagcat | ccagtgtcac | catcatggct | 180 |
| acagatacag | cccagcagag | cacagtcccc | acttccaagg | ccaacgaaat | cttggcctcg | 240 |
| gtcaaggcga | ccacccttgg | tgtatccagt | gactcaccgg | ggactacaac | cctggctcag | 300 |
| caagtctcag | gcccagtcaa | cactaccgtg | ctagaggag | gcggctcagg | caaccctact | 360 |
| accaccatcg | agagccccaa | gagcacaaaa | agtgcagaca | ccactacagt | tgcaacctcc | 420 |
| acagccacag | ctaaacctaa | caccacaagc | agccagaatg | agcagaagaa | tacaacaaac | 480 |
| tctgggggga | aaagcagcca | cagtgtgacc | acagacctca | catccactaa | ggcagaacat | 540 |
| ctgacgaccc | ctcaccctac | aagtccactt | agccccgac | aacccacttc | gacgcatcct | 600 |
| gtggccaccc | caacaagctc | gggacatgac | catcttatga | aaatttcaag | cagttcaagc | 660 |
| actgtggcta | tccctggcta | caccttcaca | agcccgggga | tgaccaccac | cctactagag | 720 |
| acagtgtttc | accatgtcag | ccaggctggt | cttgaactcc | tgacctcggg | tgatctgccc | 780 |
| accttggcct | cccaaagtgc | tgggattaca | gcgtcatcgg | ttatctcgca | aagaactcaa | 840 |
| cagacctcca | gtcagatgcc | agccagctct | acggcccctt | cctcccagga | gacagtgcag | 900 |
| cccacgagcc | cggcaacggc | attgagaaca | cctaccctgc | cagagaccat | gagctccagc | 960 |
| cccacagcag | catcaactac | ccaccgatac | cccaaaacac | cttctcccac | tgtggctcat | 1020 |
| gagagtaact | gggcaaagtg | tgaggatctt | gagacacaga | cacagagtga | aagcagctc | 1080 |
| gtcctgaacc | tcacaggaaa | caccctctgt | gcaggggcg | cttcggatga | aaattgatc | 1140 |
| tcactgatat | gccgagcagt | caaagccacc | ttcaacccgg | cccaagataa | gtgcggcata | 1200 |
| cggctggcat | ctgttccagg | aagtcagacc | gtggtcgtca | aagaaatcac | tattcacact | 1260 |
| aagctccctg | ccaaggatgt | gtacgagcgg | ctgaaggaca | aatgggatga | actaaaggag | 1320 |
| gcaggggtca | gtgacatgaa | gctaggggac | caggggccac | cggaggaggc | cgaggaccgc | 1380 |
| ttcagcatgc | ccctcatcat | caccatcgtc | tgcatggcat | cattcctgct | cctcgtggcg | 1440 |
| gccctctatg | gctgctgcca | ccagcgcctc | tcccagagga | aggaccagca | gcggctaaca | 1500 |
| gaggagctgc | agacagtgga | gaatggttac | catgacaacc | caacactgga | agtgatggag | 1560 |
| acctcttctg | agatgcagga | gaagaaggtg | gtcagcctca | acgggagct | ggggacagc | 1620 |
| tggatcgtcc | ctctggacaa | cctgaccaag | gacgacctgg | atgaggagga | agacacacac | 1680 |
| ctctag | | | | | 1686 |

<210> SEQ ID NO 11
<211> LENGTH: 1590
<212> TYPE: DNA
<213> ORGANISM: Homo sapiens

<400> SEQUENCE: 11

| | | | | | |
|---|---|---|---|---|---|
| gacgacacga | tgcgctgcgc | gctggcgctc | tcggcgctgc | tgctactgtt | gtcaacgccg | 60 |
| ccgctgctgc | cgtcgtcgcc | gtcgccgtcg | ccgtcgccct | cccagaatgc | aacccagact | 120 |
| actacggact | catctaacaa | aacagcaccg | actccagcat | ccagtgtcac | catcatggct | 180 |

-continued

```
acagatacag cccagcagag cacagtcccc acttccaagg ccaacgaaat cttggcctcg      240
gtcaaggcga ccacccttgg tgtatccagt gactcaccgg ggactacaac cctggctcag      300
caagtctcag gcccagtcaa cactaccgtg gctagaggag gcggctcagg caaccctact      360
accaccatcg agagcccaa gagcacaaaa agtgcagaca ccactacagt tgcaacctcc       420
acagccacag ctaaacctaa caccacaagc agccagaatg gagcagaaga tacaacaaac      480
tctgggggga aaagcagcca cagtgtgacc acagacctca catccactaa ggcagaacat      540
ctgacgaccc ctcaccctac aagtccactt agccccgac aacccacttc gacgcatcct       600
gtggccaccc caacaagctc gggacatgac catcttatga aaatttcaag cagttcaagc      660
actgtggcta tccctggcta caccttcaca agcccgggga tgaccaccac cctaccgtca      720
tcggttatct cgcaaagaac tcaacagacc tccagtcaga tgccagccag ctctacggcc      780
ccttcctccc aggagacagt gcagcccacg agcccggcaa cggcattgag aacacctacc      840
ctgccagaga ccatgagctc cagccccaca gcagcatcaa ctacccaccg ataccccaaa      900
acaccttctc ccactgtggc tcatgagagt aactgggcaa agtgtgagga tcttgagaca      960
cagacacaga gtgagaagca gctcgtcctg aacctcacag gaaacaccct ctgtgcaggg     1020
ggcgcttcgg atgagaaatt gatctcactg atatgccgag cagtcaaagc caccttcaac     1080
ccggcccaag ataagtgcgg catacggctg gcatctgttc caggaagtca gaccgtggtc     1140
gtcaaagaaa tcactattca cactaagctc cctgccaagg atgtgtacga gcggctgaag     1200
gacaaatggg atgaactaaa ggaggcaggg gtcagtgaca tgaagctagg ggaccagggg     1260
ccaccggagg aggccgagga ccgcttcagc atgcccctca tcatcaccat cgtctgcatg     1320
gcatcattcc tgctcctcgt ggcggccctc tatggctgct gccaccgcg cctctcccag      1380 aggaaggacc agcagcggct aacagaggag ctgcagacag tggagaatgg ttaccatgac     1440
aacccaacac tggaagtgat ggagacctct tctgagatgc aggagaagaa ggtggtcagc     1500
ctcaacgggg agctggggga cagctggatc gtccctctgg acaacctgac caaggacgac     1560
ctggatgagg aggaagacac acacctctag                                      1590
```

<210> SEQ ID NO 12
<211> LENGTH: 1584
<212> TYPE: DNA
<213> ORGANISM: Homo sapiens

<400> SEQUENCE: 12

```
gacgacacga tgcgctgcgc gctggcgctc tcggcgctgc tgttactgtt gtcaacgccg       60
ccgctgctgc cgtcggcgcc gtcgccgtcg ccctcccaga atgcaaccca gactactacg      120
gactcatcta acaaaacagc accgactcca gcatccagtg tcaccatcat ggctacagat      180
acagcccagc agagcacagt ccccacttcc aaggccaacg aaatcttggc ctcggtcaag      240
gcgaccaccc ttggtgtatc cagtgactca ccggggacta caaccctggc tcagcaagtc      300
tcaggcccag tcaacactac cgtggctaga ggaggcggct caggcaaccc tactaccacc      360
atcgagagcc ccaagagcac aaaaagtgca gacaccacta cagttgcaac ctccacagcc      420
acagctaaac ctaacaccac aagcagccag aatggagcag aagatacaac aaaactctggg     480 gggaaaagca gccacagtgt gaccacagac ctcacatcca ctaaggcaga acatctgacg      540
acccctcacc ctacaagtcc acttagcccc gacaacccca cttcgacgca tcctgtggcc      600
accccaacaa gctcgggaca tgaccatctt atgaaaattt caagcagttc aagcactgtg      660
```

| | |
|---|---|
| gctatccctg gctacacctt cacaagcccg gggatgacca ccaccctacc gtcatcggtt | 720 |
| atctcgcaaa gaactcaaca gacctccagt cagatgccag ccagctctac ggccccttcc | 780 |
| tcccaggaga cagtgcagcc cacgagcccg gcaacggcat tgagaacacc taccctgcca | 840 |
| gagaccatga gctccagccc cacagcagca tcaactaccc accgataccc aaaacacct | 900 |
| tctcccactg tggctcatga gagtaactgg gcaaagtgtg aggatcttga cacacagaca | 960 |
| cagagtgaga agcagctcgt cctgaacctc acaggaaaca ccctctgtgc agggggcgct | 1020 |
| tcggatgaga aattgatctc actgatatgc cgagcagtca aagccacctt caacccggcc | 1080 |
| caagataagt gcggcatacg gctggcatct gttccaggaa gtcagaccgt ggtcgtcaaa | 1140 |
| gaaatcacta ttcacactaa gctccctgcc aaggatgtgt acgagcggct gaaggacaaa | 1200 |
| tgggatgaac taaaggaggc aggggtcagt gacatgaagc taggggacca ggggccaccg | 1260 |
| gaggaggccg aggaccgctt cagcatgccc ctcatcatca ccatcgtctg catggcatca | 1320 |
| ttcctgctcc tcgtggcggc cctctatggc tgctgccacc agcgcctctc ccagaggaag | 1380 |
| gaccagcagc ggctaacaga ggagctgcag acagtggaga atggttacca tgacaaccca | 1440 |
| acactggaag tgatggagac ctcttctgag atgcaggaga agaaggtggt cagcctcaac | 1500 |
| ggggagctgg gggacagctg gatcgtccct ctggacaacc tgaccaagga cgacctggat | 1560 |
| gaggaggaag acacacacct ctag | 1584 |

<210> SEQ ID NO 13
<211> LENGTH: 1686
<212> TYPE: DNA
<213> ORGANISM: Homo sapiens

<400> SEQUENCE: 13

| | |
|---|---|
| gacgacacga tgcgctgcgc gctggcgctc tcggcgctgc tgctactgtt gtcaacgccg | 60 |
| ccgctgctgc cgtcgtcgcc gtcgccgtcg ccgtcgccct cccagaatgc aacccagact | 120 |
| actacggact catctaacaa aacagcaccg actccagcat ccagtgtcac catcatggct | 180 |
| acagatacag cccagcagag cacagtcccc acttccaagg ccaacgaaat cttggcctcg | 240 |
| gtcaaggcga ccaccccttgg tgtatccagt gactcaccgg ggactacaac cctggctcag | 300 |
| caagtctcag gcccagtcaa cactaccgtg gctagaggag gcggctcagg caaccctact | 360 |
| accaccatcg agagccccaa gagcacaaaa agtgcagaca ccactacagt tgcaacctcc | 420 |
| acagccacag ctaaacctaa caccacaagc agccagaatg gagcagaaga tacaacaaac | 480 |
| tctgggggga aaagcagcca cagtgtgacc acagacctca catccactaa ggcagaacat | 540 |
| ctgacgaccc ctcaccctac aagtccactt agcccccgac aacccacttc gacgcatcct | 600 |
| gtggccaccc caacaagctc gggacatgac catcttatga aaatttcaag cagttcaagc | 660 |
| actgtggcta tccctggcta caccttcaca agcccgggga tgaccaccac cctactagag | 720 |
| acagtgtttc accatgtcag ccaggctggt cttgaactcc tgacctcggg tgatctgccc | 780 |
| accttggcct cccaaagtgc tgggattaca gcgtcatcgg ttatctcgca aagaactcaa | 840 |
| cagacctcca gtcagatgcc agccagctct acggccccttt cctcccagga cagtgcag | 900 |
| cccacgagcc cggcaacggc attgagaaca cctaccctgc cagagaccat gagctccagc | 960 |
| cccacagcag catcaactac ccaccgatac ccaaaacac cttctcccac tgtggctcat | 1020 |
| gagagtaact gggcaaagtg tgaggatctt gagacacaga cacagagtga agcagctc | 1080 |
| gtcctgaacc tcacaggaaa caccctctgt gcagggggcg cttcggatga aaattgatc | 1140 |
| tcactgatat gccgagcagt caaagccacc ttcaacccgg cccaagataa gtgcggcata | 1200 |

| | |
|---|---:|
| cggctggcat ctgttccagg aagtcagacc gtggtcgtca agaaaatcac tattcacact | 1260 |
| aagctccctg ccaaggatgt gtacgagcgg ctgaaggaca atgggatga actaaaggag | 1320 |
| gcagggtca gtgacatgaa gctagggga caggggccac cggaggaggc cgaggaccgc | 1380 |
| ttcagcatgc ccctcatcat caccatcgtc tgcatggcat cattcctgct cctcgtggcg | 1440 |
| gccctctatg gctgctgcca ccagcgcctc tcccagagga aggaccagca gcggctaaca | 1500 |
| gaggagctgc agacagtgga gaatggttac catgacaacc caacactgga agtgatggag | 1560 |
| acctcttctg agatgcagga agaaggtg gtcagcctca cggggagct ggggacagc | 1620 |
| tggatcgtcc ctctggacaa cctgaccaag gacgacctgg atgaggagga agacacacac | 1680 |
| ctctag | 1686 |

<210> SEQ ID NO 14
<211> LENGTH: 1590
<212> TYPE: DNA
<213> ORGANISM: Homo sapiens

<400> SEQUENCE: 14

| | |
|---|---:|
| gacgacacga tgcgctgcgc gctggcgctc tcggcgctgc tgctactgtt gtcaacgccg | 60 |
| ccgctgctgc cgtcgtcgcc gtcgccgtcg ccgtcgccct cccagaatgc aacccagact | 120 |
| actacggact catctaacaa aacagcaccg actccagcat ccagtgtcac catcatggct | 180 |
| acagatacag cccagcagag cacagtcccc acttccaagg ccaacgaaat cttggcctcg | 240 |
| gtcaaggcga ccaccttgg tgtatccagt gactcaccgg ggactacaac cctggctcag | 300 |
| caagtctcag gcccagtcaa cactaccgtg gctagaggag gcggctcagg caaccctact | 360 |
| accaccatcg agagcccaa gagcacaaaa agtgcagaca ccactacagt tgcaacctcc | 420 |
| acagccacag ctaaacctaa caccacaagc agccagaatg gagcagaaga tacaacaaac | 480 |
| tctgggggga aaagcagcca cagtgtgacc acagacctca catccactaa ggcagaacat | 540 |
| ctgacgaccc ctcaccctac aagtccactt agccccgac aacccacttc gacgcatcct | 600 |
| gtggccaccc caacaagctc gggacatgac catcttatga aaatttcaag cagttcaagc | 660 |
| actgtggcta tccctggcta caccttcaca agcccgggga tgaccaccac cctaccgtca | 720 |
| tcggttatct cgcaaagaac tcaacagacc tccagtcaga tgccagccag ctctacggcc | 780 |
| ccttcctccc aggagacagt gcagcccacg agccggcaa cggcattgag aacacctacc | 840 |
| ctgccagaga ccatgagctc cagccccaca gcagcatcaa ctaccaccg atacccaaa | 900 |
| acaccttctc ccactgtggc tcatgagagt aactgggcaa agtgtgagga tcttgagaca | 960 |
| cagacacaga gtgagaagca gctcgtcctg aacctcacag gaaacaccct ctgtgcaggg | 1020 |
| ggcgcttcgg atgagaaatt gatctcactg atatgccgag cagtcaaagc caccttcaac | 1080 |
| ccggcccaag ataagtgcgg catacggctg gcatctgttc caggaagtca gaccgtggtc | 1140 |
| gtcaaagaaa tcactattca cactaagctc cctgccaagg atgtgtacga gcggctgaag | 1200 |
| gacaaatggg atgaactaaa ggaggcaggg gtcagtgaca tgaagctagg ggaccagggg | 1260 |
| ccaccggagg aggccgagga ccgcttcagc atgccctca tcatcaccat cgtctgcatg | 1320 |
| gcatcattcc tgctcctcgt ggcggccctc tatggctgct gccaccagcg cctctcccag | 1380 |
| aggaaggacc agcagcggct aacagaggag ctgcagacag tggagaatgg ttaccatgac | 1440 |
| aacccaacac tggaagtgat ggagacctct tctgagatgc aggagaagaa ggtggtcagc | 1500 |
| ctcaacgggg agctggggga cagctggatc gtccctctgg acaacctgac caaggacgac | 1560 | ctggatgagg aggaagacac acacctctag                                        1590

<210> SEQ ID NO 15
<211> LENGTH: 1584
<212> TYPE: DNA
<213> ORGANISM: Homo sapiens

<400> SEQUENCE: 15
gacgacacga tgcgctgcgc gctggcgctc tcggcgctgc tgttactgtt gtcaacgccg      60
ccgctgctgc cgtcggcgcc gtcgccgtcg ccctcccaga atgcaaccca gactactacg     120
gactcatcta acaaaacagc accgactcca gcatccagtg tcaccatcat ggctacagat     180
acagcccagc agagcacagt ccccacttcc aaggccaacg aaatcttggc ctcggtcaag     240
gcgaccaccc ttggtgtatc cagtgactca ccggggacta caaccctggc tcagcaagtc     300
tcaggcccag tcaacactac cgtggctaga ggaggcggct caggcaaccc tactaccacc     360
atcgagagcc ccaagagcac aaaaagtgca gacaccacta cagttgcaac ctccacagcc     420
acagctaaac ctaacaccac aagcagccag aatggagcag aagatacaac aaactctggg     480
gggaaaagca gccacagtgt gaccacagac ctcacatcca ctaaggcaga acatctgacg     540 accccctcacc ctacaagtcc acttagcccc cgacaaccca cttcgacgca tcctgtggcc     600
accccaacaa gctcgggaca tgaccatctt atgaaaattt caagcagttc aagcactgtg     660
gctatccctg gctacacctt cacaagcccg gggatgacca ccaccctacc gtcatcggtt     720
atctcgcaaa gaactcaaca gacctccagt cagatgccag ccagctctac ggcccccttcc     780 tcccaggaga cagtgcagcc cacgagcccg gcaacggcat tgagaacacc taccctgcca     840
gagaccatga gctccagccc cacagcagca tcaactaccc accgataccc caaaacacct     900
tctcccactg tggctcatga gagtaactgg gcaaagtgtg aggatcttga gacacagaca     960
cagagtgaga agcagctcgt cctgaacctc acaggaaaca ccctctgtgc aggggggcgct    1020 tcggatgaga aattgatctc actgatatgc cgagcagtca aagccacctt caacccggcc    1080
caagataagt gcggcatacg gctggcatct gttccaggaa gtcagaccgt ggtcgtcaaa    1140
gaaatcacta ttcacactaa gctccctgcc aaggatgtgt acgagcggct gaaggacaaa    1200
tgggatgaac taaaggaggc aggggtcagt gacatgaagc tagggggacca ggggccaccg    1260 gaggaggccg aggaccgctt cagcatgccc ctcatcatca ccatcgtctg catggcatca    1320
ttcctgctcc tcgtggcggc cctctatggc tgctgccacc agcgcctctc ccagaggaag    1380
gaccagcagc ggctaacaga ggagctgcag acagtggaga atggttacca tgacaaccca    1440
acactggaag tgatggagac ctcttctgag atgcaggaga agaaggtggt cagcctcaac    1500
ggggagctgg gggacagctg gatcgtccct ctggacaacc tgaccaagga cgacctggat    1560
gaggaggaag acacacacct ctag                                           1584

<210> SEQ ID NO 16
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: modified_base
<222> LOCATION: (4)..(5)

```
<223> OTHER INFORMATION: a, c, t, g, unknown or other
<220> FEATURE:
<221> NAME/KEY: modified_base
<222> LOCATION: (7)..(8)
<223> OTHER INFORMATION: a, c, t, g, unknown or other
<220> FEATURE:
<221> NAME/KEY: modified_base
<222> LOCATION: (10)..(11)
<223> OTHER INFORMATION: a, c, t, g, unknown or other
<220> FEATURE:
<221> NAME/KEY: modified_base
<222> LOCATION: (13)..(14)
<223> OTHER INFORMATION: a, c, t, g, unknown or other
<220> FEATURE:
<221> NAME/KEY: modified_base
<222> LOCATION: (16)..(17)
<223> OTHER INFORMATION: a, c, t, g, unknown or other
<220> FEATURE:
<221> NAME/KEY: modified_base
<222> LOCATION: (19)..(20)
<223> OTHER INFORMATION: a, c, t, g, unknown or other
<220> FEATURE:
<221> NAME/KEY: modified_base
<222> LOCATION: (22)..(23)
<223> OTHER INFORMATION: a, c, t, g, unknown or other
<220> FEATURE:
<221> NAME/KEY: modified_base
<222> LOCATION: (25)..(26)
<223> OTHER INFORMATION: a, c, t, g, unknown or other
<220> FEATURE:
<221> NAME/KEY: modified_base
<222> LOCATION: (28)..(29)
<223> OTHER INFORMATION: a, c, t, g, unknown or other
<220> FEATURE:
<221> NAME/KEY: modified_base
<222> LOCATION: (31)..(32)
<223> OTHER INFORMATION: a, c, t, g, unknown or other
<220> FEATURE:
<221> NAME/KEY: modified_base
<222> LOCATION: (34)..(35)
<223> OTHER INFORMATION: a, c, t, g, unknown or other
<220> FEATURE:
<221> NAME/KEY: modified_base
<222> LOCATION: (37)..(38)
<223> OTHER INFORMATION: a, c, t, g, unknown or other
<220> FEATURE:
<221> NAME/KEY: modified_base
<222> LOCATION: (40)..(41)
<223> OTHER INFORMATION: a, c, t, g, unknown or other
<220> FEATURE:
<221> NAME/KEY: modified_base
<222> LOCATION: (43)..(44)
<223> OTHER INFORMATION: a, c, t, g, unknown or other
<220> FEATURE:
<221> NAME/KEY: modified_base
<222> LOCATION: (46)..(47)
<223> OTHER INFORMATION: a, c, t, g, unknown or other
<220> FEATURE:
<221> NAME/KEY: modified_base
<222> LOCATION: (49)..(50)
<223> OTHER INFORMATION: a, c, t, g, unknown or other
<220> FEATURE:
<221> NAME/KEY: modified_base
<222> LOCATION: (52)..(53)
<223> OTHER INFORMATION: a, c, t, g, unknown or other
<220> FEATURE:
<221> NAME/KEY: modified_base
<222> LOCATION: (55)..(56)
<223> OTHER INFORMATION: a, c, t, g, unknown or other
<220> FEATURE:
<221> NAME/KEY: modified_base
<222> LOCATION: (58)..(59)
<223> OTHER INFORMATION: a, c, t, g, unknown or other

<400> SEQUENCE: 16
nnknnknnkn nknnknnknn knnknnknnk nnknnknnkn nknnknnknn knnknnknnk    60
```

```
<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Gly Gly Gly Ser Gly Gly Gly Gly Ser Gly Gly Gly Gly Ser
1               5                   10                  15

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 18

His His His His His His
1               5

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Phe Thr Phe Ser Thr Tyr Thr Met Ser
1               5                   10

<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Thr Ile Ser Gly Gly Val Ile Tyr Thr Tyr Tyr Pro Asp Ser Val Lys
1               5                   10                  15

Gly

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

His Tyr Ser Asn Tyr Glu Gly Gln Gly Met Asp Ser
1               5                   10
```